(12) United States Patent
Tyson

(10) Patent No.: US 8,993,731 B2
(45) Date of Patent: Mar. 31, 2015

(54) PD-1 ANTIBODY

(75) Inventor: Kerry Louise Tyson, Reading (GB)

(73) Assignee: UCB Biopharma SPRL, Brussels (BE)

( * ) Notice: Subject to any disclaimer, the term of this patent is extended or adjusted under 35 U.S.C. 154(b) by 0 days.

(21) Appl. No.: 13/583,999

(22) PCT Filed: Mar. 9, 2011

(86) PCT No.: PCT/EP2011/053559
§ 371 (c)(1),
(2), (4) Date: Dec. 14, 2012

(87) PCT Pub. No.: WO2011/110604
PCT Pub. Date: Sep. 15, 2011

(65) Prior Publication Data
US 2013/0095098 A1    Apr. 18, 2013

Related U.S. Application Data

(60) Provisional application No. 61/312,754, filed on Mar. 11, 2010.

(51) Int. Cl.
C07K 16/28     (2006.01)
A61K 39/395    (2006.01)
A61K 45/06     (2006.01)

(52) U.S. Cl.
CPC ......... *C07K 16/2803* (2013.01); *C07K 16/2818* (2013.01); *A61K 39/3955* (2013.01); *A61K 45/06* (2013.01); *C07K 2317/24* (2013.01); *C07K 2317/567* (2013.01); *C07K 2317/75* (2013.01); *C07K 2317/92* (2013.01); *C07K 2319/30* (2013.01)
USPC .............. 530/388.75; 530/387.3; 530/388.22; 530/391.7; 424/133.1; 424/141.1; 424/144.1; 424/154.1; 424/178.1; 536/23.53; 435/69.6; 435/70.1; 435/328; 435/331; 435/320.1

(58) Field of Classification Search
CPC ........... C07K 16/2803; C07K 16/2818; C07K 2317/24; C07K 2317/567; C07K 2317/75
See application file for complete search history.

(56) References Cited

U.S. PATENT DOCUMENTS

| | | | |
|---|---|---|---|
| 4,741,900 A | 5/1988 | Alvarez et al. | |
| 5,219,996 A | 6/1993 | Bodmer et al. | |
| 5,585,089 A | 12/1996 | Queen et al. | |
| 5,629,204 A | 5/1997 | Honjo et al. | |
| 5,667,425 A | 9/1997 | Lonberg et al. | |
| 5,698,520 A | 12/1997 | Honjo et al. | |
| 6,808,710 B1 | 10/2004 | Wood et al. | |
| 7,029,674 B2 | 4/2006 | Carreno et al. | |
| 7,101,550 B2 | 9/2006 | Wood et al. | |
| 7,105,328 B2 | 9/2006 | Wood et al. | |
| 7,432,059 B2 | 10/2008 | Freeman et al. | |
| 7,595,048 B2 | 9/2009 | Honjo et al. | |
| 7,635,757 B2 | 12/2009 | Freeman et al. | |
| 7,638,492 B2 | 12/2009 | Wood et al. | |
| 7,700,301 B2 | 4/2010 | Wood et al. | |
| 7,709,214 B2 | 5/2010 | Freeman et al. | |
| 7,722,868 B2 | 5/2010 | Freeman et al. | |
| 7,851,598 B2 | 12/2010 | Davis | |
| 2004/0033497 A1 | 2/2004 | Alarcon-Riquelme et al. | |
| 2007/0122378 A1 | 5/2007 | Freeman et al. | |
| 2009/0028857 A1 | 1/2009 | Li et al. | |
| 2009/0217401 A1 | 8/2009 | Korman et al. | |
| 2010/0035973 A1 | 2/2010 | Walker | |
| 2010/0040614 A1 | 2/2010 | Ahmed et al. | |
| 2010/0151492 A1 | 6/2010 | Ahmed et al. | |
| 2010/0266617 A1 | 10/2010 | Carven et al. | |
| 2011/0008369 A1 | 1/2011 | Finnefrock et al. | |
| 2011/0171215 A1* | 7/2011 | Davis et al. ............... | 424/133.1 |
| 2011/0177088 A1 | 7/2011 | Olive et al. | |
| 2011/0271358 A1 | 11/2011 | Freeman et al. | |
| 2012/0269806 A1 | 10/2012 | Sykes | |

FOREIGN PATENT DOCUMENTS

| | | |
|---|---|---|
| EP | 0392745 B1 | 11/1994 |
| EP | 0948544 B1 | 5/2003 |
| EP | 1090037 B1 | 11/2004 |
| WO | WO 86/01533 A1 | 3/1986 |
| WO | WO 89/00195 A1 | 1/1989 |
| WO | WO 89/01476 A1 | 2/1989 |
| WO | WO 91/09967 A1 | 7/1991 |
| WO | WO 92/02551 A1 | 2/1992 |
| WO | WO 92/22583 A2 | 12/1992 |
| WO | WO 93/06231 A1 | 4/1993 |
| WO | WO 98/20734 A1 | 5/1998 |
| WO | WO 98/25971 A1 | 6/1998 |
| WO | WO 03/031581 A2 | 4/2003 |
| WO | WO 03/048208 A2 | 6/2003 |
| WO | WO 2004/051268 A1 | 6/2004 |
| WO | WO 2004/056875 A1 | 7/2004 |
| WO | WO 2004/106377 A1 | 12/2004 |
| WO | WO 2005/003169 A2 | 1/2005 |
| WO | WO 2005/003170 A2 | 1/2005 |
| WO | WO 2005/003171 A2 | 1/2005 |
| WO | WO 2005/113605 A1 | 12/2005 |
| WO | WO 2005/117984 A2 | 12/2005 |
| WO | WO 2008/038024 A1 | 4/2008 |
| WO | WO 2009/040562 A1 | 4/2009 |
| WO | PCT/IB2009/006946 | 9/2009 |
| WO | WO 2010/029434 A1 | 3/2010 |
| WO | WO 2010/029435 A1 | 3/2010 |

OTHER PUBLICATIONS

Sequence alignment, 2014, 1 page.*

(Continued)

*Primary Examiner* — Ilia Ouspenski
(74) *Attorney, Agent, or Firm* — Saul Ewing LLP; Doreen Y. Trujillo

(57) ABSTRACT

A humanized agonistic antibody which binds human PD-1 comprising a heavy chain wherein the variable domain of the heavy chain comprises the sequence given in SEQ ID NO:1 for CDR-H1, the sequence given in SEQ ID NO: 2 for CDR-H2 and the sequence given in SEQ ID NO: 3 for CDR-H3 and the heavy chain framework region is derived from human sub-group sequence VH4 3-1 4-30.4+JH4 (SEQ ID NO: 33). The disclosure also extends to therapeutic uses of the antibody molecules, compositions and methods for producing said antibody molecules.

17 Claims, 13 Drawing Sheets

(56) References Cited

OTHER PUBLICATIONS

Agata, Y., et al., "Expression of the PD-1 antigen on the surface of stimulated mouse T and B lymphocytes", Int Immunol, vol. 8, pp. 765-772, 1996.
Altschul, S.F., et al., "Basic local alignment search tool", J. Mol. Biol,., vol. 215, No. 3, pp. 403-410, 1990.
Altschul, S.F.., et al., "gapped BLAST and PSI-BLAST: a new generation of protein database search programs", Nucleic Acids Res., vol. 25, pp. 3389-3402, 1997.
Babcook, J., et al., "A novel strategy for generating monoclonal antibodies from single, isolated lymphocytes producing antibodies of defined specificities", Proc. Natl. Acad. Sci USA, vol. 93, No. 15, pp. 7843-7848, 1996.
Chapman, A., "PEGylated antibodies and antibody fragments for improved therapy: a review", Advanced Drug Delivery Reviews, vol. 54, pp. 531-545, 2002.
Chemnitz, J.M., et al., "SHP-1 and SHP-2 associate with immunoreceptor tyrosine-based switch motif of programmed death 1 upon primary human T cell stimulation, but only receptor ligation prevents T cell activation", J Immunol, vol. 173, pp. 945-954, 2004.
Chothia, C., and Lesk, A.M., Canonical Structures for the Hypervariable Regions of Immunoglobulins, J. Mol. Biol., vol. 196, pp. 901-917, 1987.
Crameri, A., et al., "DNA shuffling of a family of genes from diverse species accelerates directed evolution", Nature, vol. 391, pp. 288-291, 1998.
Ding, H., et al., "Delivering PD-1 inhibitory signal concomitant with blocking ICOS co-stimulation suppresses lupus-like syndrome in autoimmune BXSB mice", Clinical Immunology, vol. 118, Nos. 2-3, pp. 258-267, 2006.
Dubowchik, G.M., et al., "Receptor-mediated and enzyme dependent targeting of cytotoxic anticancer drugs", Pharmacology and Therapeutics, vol. 83, No. 2, pp. 67-123, 1999.
Francisco, L.M., et al., "PD-L1 regulates the development, maintenance, and function of induced regulatory T cells", J Exp Med, vol. 206, No. 13, pp. 3015-3029, 2009.
Freeman, G., et al., "Engagement of the PD-1 Immunoinhibitory Receptor by a Novel B7 Family Member Leads to Negative Regulation of Lymphocyte Activation", J. Exp Med, vol. 192, No. 7, p. 1027-1034, 2000.
Hieter, P.A., et al., "Evolution of Human Immunoglobulin K J Region Genes", J. Biol. Chem., vol. 257, No. 3, pp. 1516-1522, 1982.
Hirata, S., et al., "Prevention of Experimental Autoimmune Encephalomyelitis by Transfer of Embryonic Stem Cell-Derived Dendritic Cells Expressing Myelin Oligodendrocyte Glycoprotein Peptide along with TRAIL or Programmed Death-1 Ligand", The Journal of Immunology, vol. 174, pp. 1888-1897, 2005.
Holliger, P., et al., "Engineered antibody fragments and the rise of single domains", Nature Biotechnology, vol. 23, No. 9, pp. 1126-1136, 2005.
Kashmiri, S.V.S., et al., "SDR grafting—a new approach to antibody humanization", Methods, vol. 36, pp. 25-34, 2005.
Keir, M., et al., "Programmed death-1 (PD-1): PD-ligand 1 interactions inhibit TCR-mediated positive selection of thymocytes", Journal of Immunology, vol. 175, No. 11, pp. 7372-7379, 2005.
Keir, M.E., et al., PD-1 and Its Ligands in Tolerance and Immunity, Annual Review of Immunology, vol. 26, pp. 677-704, 2008.
Kohler, G., & Milstein, C., "Continuous cultures of fused cells secreting antibody of predefined specificity", Nature, vol. 256, pp. 495-497, 1975.
Kroner, A., et al., "A PD-1 polymorphism is associated with disease progression in multiple sclerosis", Annals of Neurology, vol. 58, pp. 50-57, 2005.
Latchman, Y., et al., "PD-L2 is a second ligand for PD-1 and Inhibits T cell activation", Immunol, vol. 2, No. 3, pp. 261-268, 2001.
Low, N.M., et al., "Mimicking somatic hypermutation: affinity maturation of antibodies displayed on bacteriophage using a bacterial mutator strain", J. Mol. Biol., vol. 260, pp. 359-368, 1996.
Madden, T.L., et al., "Network BLAST Server Applications", Meth. Enzymol., vol. 266, pp. 131-141, 1996.
Nishimura, H., et al., "Development of Lupus-like Autoimmune Diseases by Disruption of the PD-1 Gene Encoding an ITIM Motif-Carrying Immunoreceptor", Immunity, vol. 11, pp. 141-151, 1999.
Nishimura, H., et al., "Autoimmune Dilated Cardiomyopathy in PD-1 Receptor-Deficient Mice", Science, vol. 291, No. 5502, pp. 319-322, 2001.
Okazaki, T., et al., "PD-1 and PD-1 ligands: from discovery to clinical application", International Immunology, vol. 19, No. 7, pp. 813-824, 2007.
Patten, P., et al., "Applications of DA shuffling to pharmaceuticals and vaccines", Curr. Opin. Biotechnol., vol. 8, No. 6, pp. 724-733, 1997.
Prokunina, L., et al., "A regulatory polymorphism in PDCD1 is associated with susceptibility to systemic lupus erythematosus in humans", Nat Genet, vol. 32, No. 4, pp. 666-669, 2002.
Prokunina, L., et al., "Association of the PD-1.3A Allele of the PDCDI Gene in Patients with Rheumatoid Arthritis Negative for Rheumatoid Factor and the Shared Epitope", Arthritis & Rheumatism, vol. 50, No. 6, pp. 1770-1773, 2004.
Riley, J.L., "PD-1 signaling in primary T cells", Immunological Reviews, vol. 229, No. 1, pp. 114-125, 2009.
Seko, Y., et al., "Roles of programmed death-1 (PD-1)/PD-1 ligands pathway in the development of murine acute myocarditis caused by coxsackievirus B3", Cardiovascular Reasearch, vol. 75, No. 1, pp. 158-167, 2007.
Thompson, et al., "Affinity maturation of a high-affinity human monoclonal antibody against the third hypervariable loop of human immunodeficiency virus: use of phage display to improve affinity and broaden strain reactivity", J. Mol. Biol., vol. 256, pp. 77-88, 1996.
Vaughan, et al., "Human antibodies by design", Nature Biotechnology, vol. 16, No. 6, pp. 535-539, 1998.
Verma, R., et al., "Antibody engineering: comparison of bacterial, yeast, insect and mammalian expression systems", Journal of Immunological Methods, vol. 216, Nos. 1-2, pp. 165-181, 1998.
Wang, J., et al., "Establishment of NOD-Pdcd 1-/- mice as an efficient animal model of type I diabetes", Proc Natl Acad Sci USA, vol. 102, No. 33, pp. 11823-11828, 2005.
Wang, L, et al., "Programmed cell death 1 (PD-1) and its ligand PD-L1 are required for allograft tolerance", European Journal of Immunology, vol. 37, No. 10, pp. 2983-2990, 2007.
Yang, W.P., et al., "CDR walking mutagenesis for the affinity maturation of a potent human anti-HIV-1 antibody into the picomolar range", J. Mol. Biol., vol. 254, pp. 392-403, 1995.
Zhang, J., et al., "PowerBLAST: a new network BLAST application for interactive or automated sequence analysis and annotation", Genome Research, vol. 7, No. 6, pp. 649-656, 1997.
International Search Report of International Application No. PCT/EP2011/053559 dated as mailed Aug. 17, 2011.

\* cited by examiner

Figure 1

CDRH1 GYSITSDYAWN (SEQ ID NO:1)

CDRH2 YINYSGSTSYNPSLKS (SEQ ID NO:2)

CDRH3 WIGSSAWYFDV (SEQ ID NO:3)

CDRL1 RSGQNIVHSNGNTYLE (SEQ ID NO:4)

CDRL2 KVSNRFF (SEQ ID NO:5)

CDRL3 FQGSHVPFT (SEQ ID NO:6)

Mouse Ab 948 VL region (SEQ ID NO:7)
DVLMTQTPLS LPVSLGDQAS ISCRSGQNIV HSNGNTYLEW YLQKPGQSPK
LLIYKVSNRF FGVPDRISGS GSGTDFTLKI SRVEAEDLGV YFCFQGSHVP
FTFGSGTKLE IK Mouse Ab 948 VL region ((SEQ ID NO:8)
gatgttttga tgacccaaac tccactctcc ctgcctgtca gtcttggaga
tcaagcctcc atctcttgca gatctggtca gaacattgta catagtaatg
gaaacaccta tttagaatgg tacctacaga accaggcca gtctccaaag
ctcctgatct acaaagtctc caaccgattt tttggggtcc cagacaggat
cagtggcagt ggatcaggga cagatttcac actcaagatc agcagagtgg
aggctgagga tctgggagtt tatttctgct tcaaggttc acatgttcca
ttcacgttcg gctcggggac aaagctggaa ataaaa Mouse Ab 948 VL region with signal sequence underlined and italicised (SEQ ID NO:9)
*MKLPVRLLVL* *MFWIPASSS*D VLMTQTPLSL PVSLGDQASI SCRSGQNIVH
SNGNTYLEWY LQKPGQSPKL LIYKVSNRFF GVPDRISGSG SGTDFTLKIS
RVEAEDLGVY FCFQGSHVPF TFGSGTKLEI K

Figure 2

Mouse Ab 948 VL region with signal sequence underlined and italicised (SEQ ID NO:10)

*atgaagttgc ctgttaggct gttggtgctg atgttctgga ttcctgcttc*
*cagcagt*gat gttttgatga cccaaactcc actctccctg cctgtcagtc
ttggagatca agcctccatc tcttgcagat ctggtcagaa cattgtacat
agtaatggaa acacctattt agaatggtac ctacagaaac caggccagtc
tccaaagctc ctgatctaca aagtctccaa ccgattttt ggggtcccag
acaggatcag tggcagtgga tcagggacag atttcacact caagatcagc
agagtggagg ctgaggatct gggagtttat ttctgctttc aaggttcaca
tgttccattc acgttcggct cggggacaaa gctggaaata aaa Mouse Ab 948 VH region (SEQ ID NO:11)

DVQLQESGPG LVKPSQSLSL TCTVTGYSIT SDYAWNWIRQ FPGNKLEWMG
YINYSGSTSY NPSLKSRISI TRDTSKNQFF LQLNSVTTED TATYYCARWI
GSSAWYFDVW GAGTTVTVS

Mouse Ab 948 VH region (SEQ ID NO:12)

gatgtgcagc ttcaggagtc gggacctggc ctggtgaaac cttctcagtc
tctgtccctc acctgcactg tcactggcta ctcaatcacc agtgattatg
cctggaactg gatccggcag tttccaggaa acaaactgga gtggatgggc
tacataaact acagtggtag cactagctac aacccatctc tcaaaagtcg
aatctctatc acccgagaca catccaagaa ccagttcttc ctgcagttga
attctgtgac tactgaggac acagccacat attactgtgc aagatggatc
ggtagtagcg cctggtactt cgatgtctgg ggcgcaggga ccacggtcac agtctcg Mouse Ab 948 VH region with signal sequence underlined and italicised (SEQ ID NO:13)

*MRVLILLWLF TAFPGILS*DV QLQESGPGLV KPSQSLSLTC TVTGYSITSD
YAWNWIRQFP GNKLEWMGYI NYSGSTSYNP SLKSRISITR DTSKNQFFLQ
LNSVTTEDTA TYYCARWIGS SAWYFDVWGA GTTVTVS

Figure 3

Mouse Ab 948 VH region with signal sequence underlined and italicised (SEQ ID NO:14)

*atgagagtgc tgattctttt gtggctgttc acagcctttc ctggtatcct*
*gtct*gatgtg cagcttcagg agtcgggacc tggcctggtg aaaccttctc
agtctctgtc cctcacctgc actgtcactg gctactcaat caccagtgat
tatgcctgga actggatccg gcagtttcca ggaaacaaac tggagtggat
gggctacata aactacagtg gtagcactag ctacaaccca tctctcaaaa
gtcgaatctc tatcacccga gacacatcca gaaccagtt cttcctgcag
ttgaattctg tgactactga ggacacagcc acatattact gtgcaagatg
gatcggtagt agcgcctggt acttcgatgt ctggggcgca gggaccacgg
tcacagtctc g 948.g1 VL (SEQ ID NO:15)

DVLMTQTPLS LSVTPGQPAS ISCRSGQNIV HSNGNTYLEW YLQKPGQSPK
LLIYKVSNRF FGVPDRISGS GSGTDFTLKI SRVEAEDVGV YFCFQGSHVP
FTFGQGTKLE IK 948.g1 VL (SEQ ID NO:16)

gacgtgctga tgacccagac cccctgtca cttagcgtga ctcctggcca
acctgcctca atttcctgtc gctccggtca gaatatcgtg cactctaacg
ggaacaccta cttggagtgg tatctccaaa agcctggcca gagcccaaag
ctgctgatct acaaggtctc caatcggttc tttggcgtgc ctgacagaat
tagtggtagc ggatccggaa ctgacttcac cctgaaaatc tcacgggtgg
aagctgaaga tgtcggcgtg tatttctgct tccaaggctc ccacgttccc
tttacgtttg gacagggcac caaactggag ataaag 948.g1 VL with signal sequence underlined and italicised (SEQ ID NO:17)

*MSVPTQVLGL LLLWLTDARC* DVLMTQTPLS LSVTPGQPAS ISCRSGQNIV
HSNGNTYLEW YLQKPGQSPK LLIYKVSNRF FGVPDRISGS GSGTDFTLKI
SRVEAEDVGV YFCFQGSHVP FTFGQGTKLE IK

Figure 4

948.g1 VL with signal sequence underlined and italicised (SEQ ID NO:18)

*atgagcgtcc caacacaagt tcttgggctc cttctgctct ggcttactga*
*tgcaagatgc* gacgtgctga tgacccagac accccctgtca cttagcgtga
ctcctggcca acctgcctca atttcctgtc gctccggtca gaatatcgtg
cactctaacg ggaacaccta cttggagtgg tatctccaaa agcctggcca
gagcccaaag ctgctgatct acaaggtctc caatcggttc tttggcgtgc
ctgacagaat tagtggtagc ggatccggaa ctgacttcac cctgaaaatc
tcacgggtgg aagctgaaga tgtcggcgtg tatttctgct tccaaggctc
ccacgttccc tttacgtttg gacagggcac caaactggag ataaag 948.g1 light chain (V + constant) (SEQ ID NO:19)

DVLMTQTPLS LSVTPGQPAS ISCRSGQNIV HSNGNTYLEW YLQKPGQSPK
LLIYKVSNRF FGVPDRISGS GSGTDFTLKI SRVEAEDVGV YFCFQGSHVP
FTFGQGTKLE IKRTVAAPSV FIFPPSDEQL KSGTASVVCL LNNFYPREAK
VQWKVDNALQ SGNSQESVTE QDSKDSTYSL SSTLTLSKAD YEKHKVYACE
VTHQGLSSPV TKSFNRGEC

Figure 5

948.g1 light chain (V + constant) (SEQ ID NO:20)

gacgtgctga tgacccagac acccctgtca cttagcgtga ctcctggcca
acctgcctca atttcctgtc gctccggtca gaatatcgtg cactctaacg
ggaacaccta cttggagtgg tatctccaaa agcctggcca gagcccaaag
ctgctgatct acaaggtctc caatcggttc tttggcgtgc ctgacagaat
tagtggtagc ggatccggaa ctgacttcac cctgaaaatc tcacgggtgg
aagctgaaga tgtcggcgtg tatttctgct tccaaggctc ccacgttccc
tttacgtttg gacagggcac caaactggag ataaagcgta cggtagcggc
cccatctgtc ttcatcttcc cgccatctga tgagcagttg aaatctggaa
ctgcctctgt tgtgtgcctg ctgaataact ctatcccag agaggccaaa
gtacagtgga aggtggataa cgccctccaa tcgggtaact cccaggagag
tgtcacagag caggacagca aggacagcac ctacagcctc agcagcaccc
tgacgctgag caaagcagac tacgagaaac acaaagtcta cgcctgcgaa
gtcacccatc agggcctgag ctcgcccgtc acaaagagct caacaggg agagtgt 948.g1 light chain with signal sequence underlined and italicised (SEQ ID NO:21)

*MSVPTQVLGL LLLWLTDARC* DVLMTQTPLS LSVTPGQPAS ISCRSGQNIV
HSNGNTYLEW YLQKPGQSPK LLIYKVSNRF FGVPDRISGS GSGTDFTLKI
SRVEAEDVGV YFCFQGSHVP FTFGQGTKLE IKRTVAAPSV FIFPPSDEQL
KSGTASVVCL LNNFYPREAK VQWKVDNALQ SGNSQESVTE QDSKDSTYSL
SSTLTLSKAD YEKHKVYACE VTHQGLSSPV TKSFNRGEC

Figure 6

948.g1 light chain with signal sequence underlined and italicised (SEQ ID NO:22)

*atgagcgtcc caacacaagt tcttgggctc cttctgctct ggcttactga*
*tgcaagatgc* gacgtgctga tgacccagac acccctgtca cttagcgtga
ctcctggcca acctgcctca atttcctgtc gctccggtca gaatatcgtg
cactctaacg ggaacaccta cttggagtgg tatctccaaa agcctggcca
gagcccaaag ctgctgatct acaaggtctc caatcggttc tttggcgtgc
ctgacagaat tagtggtagc ggatccggaa ctgacttcac cctgaaaatc
tcacgggtgg aagctgaaga tgtcggcgtg tatttctgct tccaaggctc
ccacgttccc tttacgtttg gacagggcac caaactggag ataaagcgta
cggtagcggc cccatctgtc ttcatcttcc cgccatctga tgagcagttg
aaatctggaa ctgcctctgt tgtgtgcctg ctgaataact tctatcccag
agaggccaaa gtacagtgga aggtggataa cgccctccaa tcgggtaact
cccaggagag tgtcacagag caggacagca aggacagcac ctacagcctc
agcagcaccc tgacgctgag caaagcagac tacgagaaac acaaagtcta
cgcctgcgaa gtcacccatc agggcctgag ctcgcccgtc acaaagagct
tcaacagggg agagtgt 948.g1 VH (SEQ ID NO:23)

EVQLQESGPG LVKPSQTLSL TCTVTGYSIT SDYAWNWIRQ PPGKKLEWMG
YINYSGSTSY NPSLKSRVTI SRDTSKNQFS LKLSSVTAAD TAVYYCARWI
GSSAWYFDVW GQGTLVTVS 948.g1 VH (SEQ ID NO:24)

gaagttcagc tgcaagaatc cggccctgga ctcgtgaaac caagccagac
actgagcctg acttgcaccg tcactggcta tagcatcacc agcgattacg
cctggaactg gataaggcag ccacctggaa agaagctgga gtggatgggc
tacatcaact actccggaag cacgtcctac aatccctcac ttaagagcag
agtcacaatc tcacgagaca cctccaagaa ccagttctcc ctgaaactga
gctccgttac tgccgctgat actgccgtgt actattgtgc aaggtggatt
gggagctcag cttggtattt cgacgtttgg ggacaaggca cacttgtgac cgtctcg

Figure 7

948.g1 VH with signal sequence underlined and italicised (SEQ ID NO:25)

*MEWSWVFLFF* *LSVTTGVHSE* VQLQESGPGL VKPSQTLSLT CTVTGYSITS
DYAWNWIRQP PGKKLEWMGY INYSGSTSYN PSLKSRVTIS RDTSKNQFSL
KLSSVTAADT AVYYCARWIG SSAWYFDVWG QGTLVTVS 948.g1 VH with signal sequence underlined and italicised (SEQ ID NO:26)

*atggagtgga* *gctgggtctt* *tctcttcttt* *ctctccgtga* *ctaccggtgt*
*gcactcc*gaa gttcagctgc aagaatccgg ccctggactc gtgaaccaa
gccagacact gagcctgact tgcaccgtca ctggctatag catcaccagc
gattacgcct ggaactggat aaggcagcca cctggaaaga gctggagtg
gatgggctac atcaactact ccggaagcac gtcctacaat ccctcactta
agagcagagt cacaatctca cgagacacct ccaagaacca gttctccctg
aaactgagct ccgttactgc cgctgatact gccgtgtact attgtgcaag
gtggattggg agctcagctt ggtatttcga cgtttgggga caaggcacac
ttgtgaccgt ctcg 948.g1 heavy chain (V + constant – hu IgG4P) (SEQ ID NO:27)

EVQLQESGPG LVKPSQTLSL TCTVTGYSIT SDYAWNWIRQ PPGKKLEWMG
YINYSGSTSY NPSLKSRVTI SRDTSKNQFS LKLSSVTAAD TAVYYCARWI
GSSAWYFDVW GQGTLVTVSS ASTKGPSVFP LAPCSRSTSE STAALGCLVK
DYFPEPVTVS WNSGALTSGV HTFPAVLQSS GLYSLSSVVT VPSSSLGTKT
YTCNVDHKPS NTKVDKRVES KYGPPCPPCP APEFLGGPSV FLFPPKPKDT
LMISRTPEVT CVVVDVSQED PEVQFNWYVD GVEVHNAKTK PREEQFNSTY
RVVSVLTVLH QDWLNGKEYK CKVSNKGLPS SIEKTISKAK GQPREPQVYT
LPPSQEEMTK NQVSLTCLVK GFYPSDIAVE WESNGQPENN YKTTPPVLDS
DGSFFLYSRL TVDKSRWQEG NVFSCSVMHE ALHNHYTQKS LSLSLGK

Figure 8

948.g1 heavy chain (V + constant – hu IgG4P, exons underlined) (SEQ ID NO:28)

<u>gaagttcagc tgcaagaatc cggccctgga ctcgtgaaac caagccagac actgagcctg</u>
<u>acttgcaccg tcactggcta tagcatcacc agcgattacg cctggaactg gataaggcag</u>
<u>ccacctggaa agaagctgga gtggatgggc tacatcaact actccggaag cacgtcctac</u>
<u>aatccctcac ttaagagcag agtcacaatc tcacgagaca cctccaagaa ccagttctcc</u>
<u>ctgaaactga gctccgttac tgccgctgat actgccgtgt actattgtgc aaggtggatt</u>
<u>gggagctcag cttggtattt cgacgtttgg ggacaaggca cacttgtgac cgtctcgagc</u>
<u>gcttctacaa agggcccatc cgtcttcccc ctggcgccct gctccaggag cacctccgag</u>
<u>agcacagccg ccctgggctg cctggtcaag gactacttcc ccgaaccggt gacggtgtcg</u>
<u>tggaactcag gcgccctgac cagcggcgtg cacaccttcc cggctgtcct acagtcctca</u>
<u>ggactctact ccctcagcag cgtggtgacc gtgcctcca gcagcttggg cacgaagacc</u>
<u>tacacctgca acgtagatca caagcccagc aacaccaagg tggacaagag agttggtgag</u>
aggccagcac agggagggag ggtgtctgct ggaagccagg ctcagccctc ctgcctggac
gcaccccggc tgtgcagccc cagcccaggg cagcaaggca tgccccatct gtctcctcac
ccggaggcct ctgaccaccc cactcatgcc cagggagagg gtcttctgga tttttccacc
aggctccggg cagccacagg ctggatgccc ctaccccagg ccctgcgcat acaggggcag
gtgctgcgct cagacctgcc aagagccata tccgggagga ccctgcccct gacctaagcc
caccccaaag gccaaactct ccactccctc agctcagaca ccttctctcc tcccagatct
gagtaactcc caatcttctc tctgcag<u>agt ccaaatatgg tccccatgc ccaccatgcc</u>
<u>caggtaagcc aaccc</u>aggcc tcgccctcca gctcaaggcg gacaggtgc cctagagtag
cctgcatcca gggacaggcc ccagccgggt gctgacgcat ccacctccat ctcttcctca
g<u>cacctgagt tcctgggggg accatcagtc ttcctgttcc cccaaaacc caaggacact</u>
<u>ctcatgatct cccggacccc tgaggtcacg tgcgtggtgg tggacgtgag ccaggaagac</u>
<u>cccgaggtcc agttcaactg gtacgtggat ggcgtggagg tgcataatgc caagacaaag</u>
<u>ccgcgggagg agcagttcaa cagcacgtac cgtgtggtca gcgtcctcac cgtcctgcac</u>
<u>caggactggc tgaacggcaa ggagtacaag tgcaaggtct ccaacaaagg cctcccgtcc</u>
<u>tccatcgaga aaaccatctc caaagccaaa g</u>gtgggaccc acggggtgcg agggccacat
ggacagaggt cagctcggcc caccctctgc cctgggagtg accgctgtgc caacctctgt
ccctacaggg cagccccgag agccacaggt gtacaccctg cccccatccc aggaggagat
gaccaagaac caggtcagcc tgacctgcct ggtcaaaggc ttctacccca gcgacatcgc
cgtggagtgg gagagcaatg ggcagccgga gaacaactac aagaccacgc ctcccgtgct
ggactccgac ggctccttct tcctctacag caggctaacc gtggacaaga gcaggtggca
ggaggggaat gtcttctcat gctccgtgat gcatgaggct ctgcacaacc actacacaca
gaagagcctc tccctgtctc tgggtaaa

Figure 9

948.g1 heavy chain (V + constant – hu IgG4P) with signal sequence underlined and italicised (SEQ ID NO:29)

*MEWSWVFLFF LSVTTGVHS*E VQLQESGPGL VKPSQTLSLT CTVTGYSITS
DYAWNWIRQP PGKKLEWMGY INYSGSTSYN PSLKSRVTIS RDTSKNQFSL
KLSSVTAADT AVYYCARWIG SSAWYFDVWG QGTLVTVSSA STKGPSVFPL
APCSRSTSES TAALGCLVKD YFPEPVTVSW NSGALTSGVH TFPAVLQSSG
LYSLSSVVTV PSSSLGTKTY TCNVDHKPSN TKVDKRVESK YGPPCPPCPA
PEFLGGPSVF LFPPKPKDTL MISRTPEVTC VVVDVSQEDP EVQFNWYVDG
VEVHNAKTKP REEQFNSTYR VVSVLTVLHQ DWLNGKEYKC KVSNKGLPSS
IEKTISKAKG QPREPQVYTL PPSQEEMTKN QVSLTCLVKG FYPSDIAVEW
ESNGQPENNY KTTPPVLDSD GSFFLYSRLT VDKSRWQEGN VFSCSVMHEA
LHNHYTQKSL SLSLGK

Figure 10

948.g1 heavy chain (V + constant – hu IgG4P, exons underlined) with signal sequence underlined and italicised (SEQ ID NO:30)

*atggagtgga gctgggtctt tctcttcttt ctctccgtga ctaccggtgt gcactccgaa*
gttcagctgc aagaatccgg ccctggactc gtgaaccaa gccagacact gagcctgact
tgcaccgtca ctggctatag catcaccagc gattacgcct ggaactggat aaggcagcca
cctggaaaga agctggagtg gatgggctac atcaactact ccggaagcac gtcctacaat
ccctcactta agagcagagt cacaatctca cgagacacct caagaacca gttctccctg
aaactgagct ccgttactgc cgctgatact gccgtgtact attgtgcaag gtggattggg
agctcagctt ggtatttcga cgtttgggga caaggcacac ttgtgaccgt ctcgagcgct
tctacaaagg gcccatccgt cttccccctg gcgcctgct ccaggagcac ctccgagagc
acagccgccc tgggctgcct ggtcaaggac tacttcccg aaccggtgac ggtgtcgtgg
aactcaggcg ccctgaccag cggcgtgcac accttcccgg ctgtcctaca gtcctcagga
ctctactccc tcagcagcgt ggtgaccgtg cctccagca gcttgggcac gaagacctac
acctgcaacg tagatcacaa gccagcaac accaaggtgg acaagagagt tggtgagagg
ccagcacagg gagggagggt gtctgctgga agccaggctc agccctcctg cctggacgca
ccccggctgt gcagccccag cccagggcag caaggcatgc cccatctgtc tcctcacccg
gaggcctctg accacccac tcatgccag ggagagggtc ttctggattt ttccaccagg
ctccgggcag ccacaggctg gatgcccta cccaggccc tgcgcataca ggggcaggtg
ctgcgctcag acctgccaag agccatatcc gggaggaccc tgccctgac ctaagccac
cccaaaggcc aaactctcca ctccctcagc tcagacacct tctctcctcc cagatctgag
taactcccaa tcttctctct gcagagtcca aatatggtcc cccatgccca ccatgcccag
gtaagccaac ccaggcctcg ccctccagct caaggcggga caggtgccct agagtagcct
gcatccaggg acaggcccca gccgggtgct gacgcatcca cctccatctc ttcctcagca
cctgagttcc tggggggacc atcagtcttc ctgttccccc caaaacccaa ggacactctc
atgatctccc ggacccctga ggtcacgtgc gtggtggtgg acgtgagcca ggaagacccc
gaggtccagt tcaactggta cgtggatggc gtggaggtgc ataatgccaa gacaaagccg
cgggaggagc agttcaacag cacgtaccgt gtggtcagcg tcctcaccgt cctgcaccag
gactggctga acggcaagga gtacaagtgc aaggtctcca caaaggcct cccgtcctcc
atcgagaaaa ccatctccaa agccaaaggt gggacccacg gggtgcgagg gccacatgga
cagaggtcag ctcggccac cctctgcct gggagtgacc gctgtgccaa cctctgtccc
tacagggcag ccccgagagc cacaggtgta caccctgccc catcccagg aggagatgac
caagaaccag gtcagcctga cctgcctggt caaaggcttc taccccagcg acatcgccgt
ggagtgggag agcaatgggc agccggagaa caactacaag accacgcctc ccgtgctgga
ctccgacggc tccttcttcc tctacagcag gctaaccgtg gacaagagca ggtggcagga
ggggaatgtc ttctcatgct ccgtgatgca tgaggctctg cacaaccact acacacagaa
gagcctctcc ctgtctctgg gtaaa

Figure 11

Human VK2 4-1-(1) A18 JK2 acceptor framework (SEQ ID NO:31)

DIVMTQTPLS LSVTPGQPAS ISCKSSQSLL HSDGKTYLYW YLQKPGQSPQ
LLIYEVSSRF SGVPDRFSGS GSGTDFTLKI SRVEAEDVGV YYCMQGIHLP
YTFGQGTKLE IK

Human VK2 4-1-(1) A18 JK2 acceptor framework (SEQ ID NO:32)

gatattgtga tgacccagac tccactctct ctgtccgtca ccctggaca
gccggcctcc atctcctgca agtctagtca gagcctcctg catagtgatg
gaaagaccta tttgtattgg tacctgcaga agccaggcca gtctccacag
ctcctaatct atgaagtttc cagccggttc tctggagtgc cagataggtt
cagtggcagc gggtcaggga cagatttcac actgaaaatc agccgggtgg
aggctgagga tgttggggtt tattactgca tgcaaggtat acaccttcct
tacactttg gccaggggac caagctggag atcaaa Human VH4 3-1 4-30.4 JH4 acceptor framework (SEQ ID NO:33)

QVQLQESGPG LVKPSQTLSL TCTVSGGSIS SGDYYWSWIR QPPGKGLEWI
GYIYYSGSTY YNPSLKSRVT ISVDTSKNQF SLKLSSVTAA DTAVYYCARY
FDYWGQGTLV TVS

Human VH4 3-1 4-30.4 JH4 acceptor framework (SEQ ID NO:34)

caggtgcagc tgcaggagtc gggcccagga ctggtgaagc cttcacagac
cctgtccctc acctgcactg tctctggtgg ctccatcagc agtggtgatt
actactggag ttggatccgc cagccccag ggaagggcct ggagtggatt
gggtacatct attacagtgg gagcacctac tacaacccgt ccctcaagag
tcgagttacc atatcagtag acacgtccaa gaaccagttc tccctgaagc
tgagctctgt gactgccgca gacacggccg tgtattactg tgccagatac
tttgactact ggggccaggg aaccctggtc accgtctcc

Figure 13

LIGHT CHAIN Graft 948

DVLMTQTPLSLPVSLGDQASISCRSGQNIVHSNGNTYLEWYLQKPGQSPKLLIYKVSNRFFGVPDRISGSGSGTDFTLKISRVEAEDLGVYFCFQGSHVPFTFGSGTKLEIK 1

|| ||||| || ||| ||| ||| | ||| | | | – – – – – – – –

DIVMTQTPLSLSVTPGQPASISCKSSQSLLHSDGKTYLIYWYLQKPGQSPQLLIYEVSSRFSGVPDRFSGSGSGTDFTLKISRVEAEDVGVYYCMQGIHLPYTFGQGTKLEIK 2

|| – – – – –

DVLMTQTPLSLSVTPGQPASISCRSGQNIVHSNGNTYLEWYLQKPGQSPKLLIYKVSNRFFGVPDRISGSGSGTDFTLKISRVEAEDVGVYFFQGSHVPFTFGQGTKLEIK 3

HEAVY CHAIN Graft 948

DVQLQESGPGLVKPSQSLSLTCTVTGYSITS-DYAWNWIRQFPGNKLEWMGYINYSGSTSYNPSLKSRISITRDTSKNQFFLQLNSVTTEDTATYYCARWIGSSAWYFDVWGAGTTVTVS 4

| – – ||| ||| | ||| ||| – – | – – ||| |

QVQLQESGPGLVKPSQTLSLTCTVSGGSISSGDYYWSWIRQPPGKGLEWIGYIYYSGSTYYNPSLKSRVTISVDTSKNQFSLKLSSVTAADTAVYYCAR--------YFDYWGQGTLVTVS 5

– – –

EVQLQESGPGLVKPSQTLSLTCTVTGYSITS-DYAWNWIRQPPGKKLEWMGYINYSGSTSYNPSLKSRVTIISRDTSKNQFSLKLSSVTAADTAVYYCARWIGSSAWYFDV**WGQGTLVTVS 6

Legend

1 = 948 Mouse variable light chain sequence

2 = VK24-1-1A18

3 = 948.g1 Humanized graft of 948 variable light chain

4 = 948 Mouse variable heavy chain sequence

5 = VH4 3-1 4-30.4

6 = 948.g1 Humanized graft of 948 variable heavy chain

CDRs are shown in bold/underlined

For 948.g1 light chain, donor residues are shown in bold/italic: V2, L3, K45, I62 and F87

For 948.g1 heavy chain, donor residues are shown in bold/italic: T25, K44, M48 and R71

SEQUENCE LISTING

```
<160> NUMBER OF SEQ ID NOS: 36

<210> SEQ ID NO 1
<211> LENGTH: 11
<212> TYPE: PRT
<213> ORGANISM: Artificial
<220> FEATURE:
<223> OTHER INFORMATION: CDRH1

<400> SEQUENCE: 1

Gly Tyr Ser Ile Thr Ser Asp Tyr Ala Trp Asn
1               5                   10

<210> SEQ ID NO 2
<211> LENGTH: 16
<212> TYPE: PRT
<213> ORGANISM: Artificial
<220> FEATURE:
<223> OTHER INFORMATION: CDRH2

<400> SEQUENCE: 2

Tyr Ile Asn Tyr Ser Gly Ser Thr Ser Tyr Asn Pro Ser Leu Lys Ser
1               5                   10                  15

<210> SEQ ID NO 3
<211> LENGTH: 11
<212> TYPE: PRT
<213> ORGANISM: Artificial
<220> FEATURE:
<223> OTHER INFORMATION: CDRH3

<400> SEQUENCE: 3

Trp Ile Gly Ser Ser Ala Trp Tyr Phe Asp Val
1               5                   10

<210> SEQ ID NO 4
<211> LENGTH: 16
<212> TYPE: PRT
```

<213> ORGANISM: Artificial
<220> FEATURE:
<223> OTHER INFORMATION: CDRL1

<400> SEQUENCE: 4

Arg Ser Gly Gln Asn Ile Val His Ser Asn Gly Asn Thr Tyr Leu Glu
1               5                   10                  15

<210> SEQ ID NO 5
<211> LENGTH: 7
<212> TYPE: PRT
<213> ORGANISM: Artificial
<220> FEATURE:
<223> OTHER INFORMATION: CDRL2

<400> SEQUENCE: 5

Lys Val Ser Asn Arg Phe Phe
1               5

<210> SEQ ID NO 6
<211> LENGTH: 9
<212> TYPE: PRT
<213> ORGANISM: Artificial
<220> FEATURE:
<223> OTHER INFORMATION: CDRL3

<400> SEQUENCE: 6

Phe Gln Gly Ser His Val Pro Phe Thr
1               5

<210> SEQ ID NO 7
<211> LENGTH: 112
<212> TYPE: PRT
<213> ORGANISM: Artificial
<220> FEATURE:
<223> OTHER INFORMATION: Mouse Ab 948 VL region

<400> SEQUENCE: 7

Asp Val Leu Met Thr Gln Thr Pro Leu Ser Leu Pro Val Ser Leu Gly
1               5                   10                  15

Asp Gln Ala Ser Ile Ser Cys Arg Ser Gly Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Phe Gly Val Pro
    50                  55                  60

Asp Arg Ile Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Ser His Val Pro Phe Thr Phe Gly Ser Gly Thr Lys Leu Glu Ile Lys
                100                 105                 110

<210> SEQ ID NO 8
<211> LENGTH: 336
<212> TYPE: DNA
<213> ORGANISM: Artificial
<220> FEATURE:
<223> OTHER INFORMATION: Mouse Ab 948 VL region

<400> SEQUENCE: 8
gatgttttga tgacccaaac tccactctcc ctgcctgtca gtcttggaga tcaagcctcc      60
atctcttgca gatctggtca gaacattgta catagtaatg gaaacaccta tttagaatgg     120

```
tacctacaga aaccaggcca gtctccaaag ctcctgatct acaaagtctc caaccgattt       180
tttggggtcc cagacaggat cagtggcagt ggatcaggga cagatttcac actcaagatc       240
agcagagtgg aggctgagga tctgggagtt tatttctgct ttcaaggttc acatgttcca       300
ttcacgttcg gctcggggac aaagctggaa ataaaa                                 336

<210> SEQ ID NO 9
<211> LENGTH: 131
<212> TYPE: PRT
<213> ORGANISM: Artificial
<220> FEATURE:
<223> OTHER INFORMATION: Mouse Ab 948 VL

<400> SEQUENCE: 9

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
                20                  25                  30

Ser Leu Gly Asp Gln Ala Ser Ile Ser Cys Arg Ser Gly Gln Asn Ile
            35                  40                  45

Val His Ser Asn Gly Asn Thr Tyr Leu Glu Trp Tyr Leu Gln Lys Pro
        50                  55                  60

Gly Gln Ser Pro Lys Leu Leu Ile Tyr Lys Val Ser Asn Arg Phe Phe
65                  70                  75                  80

Gly Val Pro Asp Arg Ile Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Phe Gln Gly Ser His Val Pro Phe Thr Phe Gly Ser Gly Thr Lys Leu
        115                 120                 125

Glu Ile Lys
    130

<210> SEQ ID NO 10
<211> LENGTH: 393
<212> TYPE: DNA
<213> ORGANISM: Artificial
<220> FEATURE:
<223> OTHER INFORMATION: Mouse Ab 948 VL region with signal sequence

<400> SEQUENCE: 10
atgaagttgc ctgttaggct gttggtgctg atgttctgga ttcctgcttc cagcagtgat       60
gttttgatga cccaaactcc actctccctg cctgtcagtc ttggagatca agcctccatc       120
tcttgcagat ctggtcagaa cattgtacat agtaatggaa acacctattt agaatggtac       180
ctacagaaac caggccagtc tccaaagctc ctgatctaca agtctccaa ccgattttt        240 ggggtcccag acaggatcag tggcagtgga tcagggacag atttcacact caagatcagc      300
agagtggagg ctgaggatct gggagtttat ttctgctttc aaggttcaca tgttccattc      360
acgttcggct cggggacaaa gctggaaata aaa                                   393

<210> SEQ ID NO 11
<211> LENGTH: 119
<212> TYPE: PRT
<213> ORGANISM: Artificial
<220> FEATURE:
<223> OTHER INFORMATION: Mouse Ab 948 VH region

<400> SEQUENCE: 11
```

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Asn Tyr Ser Gly Ser Thr Ser Tyr Asn Pro Ser Leu
50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Trp Ile Gly Ser Ser Ala Trp Tyr Phe Asp Val Trp Gly Ala
            100                 105                 110

Gly Thr Thr Val Thr Val Ser
            115

<210> SEQ ID NO 12
<211> LENGTH: 357
<212> TYPE: DNA
<213> ORGANISM: Artificial
<220> FEATURE:
<223> OTHER INFORMATION: Mouse Ab 948 VH region

<400> SEQUENCE: 12
gatgtgcagc ttcaggagtc gggacctggc ctggtgaaac cttctcagtc tctgtccctc      60
acctgcactg tcactggcta ctcaatcacc agtgattatg cctggaactg gatccggcag     120
tttccaggaa acaaactgga gtggatgggc tacataaact acagtggtag cactagctac     180
aacccatctc tcaaaagtcg aatctctatc acccgagaca catccaagaa ccagttcttc     240
ctgcagttga attctgtgac tactgaggac acagccacat attactgtgc aagatggatc     300
ggtagtagcg cctggtactt cgatgtctgg ggcgcaggga ccacggtcac agtctcg       357

<210> SEQ ID NO 13
<211> LENGTH: 137
<212> TYPE: PRT
<213> ORGANISM: Artificial
<220> FEATURE:
<223> OTHER INFORMATION: Mouse Ab 948 VH region with signal sequence

<400> SEQUENCE: 13

Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Tyr Ala Trp Asn Trp Ile Arg Gln Phe Pro Gly Asn Lys Leu
    50                  55                  60

Glu Trp Met Gly Tyr Ile Asn Tyr Ser Gly Ser Thr Ser Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Ala Arg Trp Ile Gly Ser Ser Ala Trp Tyr Phe Asp Val Trp

```
              115                 120                 125
Gly Ala Gly Thr Thr Val Thr Val Ser
        130                 135

<210> SEQ ID NO 14
<211> LENGTH: 411
<212> TYPE: DNA
<213> ORGANISM: Artificial
<220> FEATURE:
<223> OTHER INFORMATION: Mouse Ab 948 VH region with signal sequence

<400> SEQUENCE: 14
atgagagtgc tgattctttt gtggctgttc acagcctttc ctggtatcct gtctgatgtg     60
cagcttcagg agtcgggacc tggcctggtg aaaccttctc agtctctgtc cctcacctgc    120
actgtcactg ctactcaat caccagtgat tatgcctgga actggatccg gcagtttcca    180
ggaaacaaac tggagtggat gggctacata aactacagtg gtagcactag ctacaaccca    240
tctctcaaaa gtcgaatctc tatcacccga gacacatcca agaaccagtt cttcctgcag    300
ttgaattctg tgactactga ggacacagcc acatattact gtgcaagatg gatcggtagt    360
agcgcctggt acttcgatgt ctggggcgca gggaccacgg tcacagtctc g             411

<210> SEQ ID NO 15
<211> LENGTH: 112
<212> TYPE: PRT
<213> ORGANISM: Artificial
<220> FEATURE:
<223> OTHER INFORMATION: 948.g1 VL

<400> SEQUENCE: 15

Asp Val Leu Met Thr Gln Thr Pro Leu Ser Leu Ser Val Thr Pro Gly
1               5                  10                  15

Gln Pro Ala Ser Ile Ser Cys Arg Ser Gly Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Phe Gly Val Pro
    50                  55                  60

Asp Arg Ile Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Ser His Val Pro Phe Thr Phe Gly Gln Gly Thr Lys Leu Glu Ile Lys
            100                 105                 110

<210> SEQ ID NO 16
<211> LENGTH: 336
<212> TYPE: DNA
<213> ORGANISM: Artificial
<220> FEATURE:
<223> OTHER INFORMATION: 948.g1 VL

<400> SEQUENCE: 16
gacgtgctga tgacccagac acccctgtca cttagcgtga ctcctggcca acctgcctca     60
atttcctgtc gctccggtca gaatatcgtg cactctaacg gaacaccta cttggagtgg    120 tatctccaaa agcctggcca gagcccaaag ctgctgatct acaaggtctc aatcggttc    180 tttggcgtgc ctgacagaat tagtggtagc ggatccggaa ctgacttcac cctgaaaatc    240
tcacgggtgg aagctgaaga tgtcggcgtg tatttctgct tccaaggctc ccacgttccc    300
```
tttacgtttg acagggcac caaactggag ataaag          336

<210> SEQ ID NO 17
<211> LENGTH: 132
<212> TYPE: PRT
<213> ORGANISM: Artificial
<220> FEATURE:
<223> OTHER INFORMATION: 948.g1 VL with signal sequence

<400> SEQUENCE: 17

Met Ser Val Pro Thr Gln Val Leu Gly Leu Leu Leu Trp Leu Thr
1               5                   10                  15

Asp Ala Arg Cys Asp Val Leu Met Thr Gln Thr Pro Leu Ser Leu Ser
            20                  25                  30

Val Thr Pro Gly Gln Pro Ala Ser Ile Ser Cys Arg Ser Gly Gln Asn
        35                  40                  45

Ile Val His Ser Asn Gly Asn Thr Tyr Leu Glu Trp Tyr Leu Gln Lys
    50                  55                  60

Pro Gly Gln Ser Pro Lys Leu Leu Ile Tyr Lys Val Ser Asn Arg Phe
65                  70                  75                  80

Phe Gly Val Pro Asp Arg Ile Ser Gly Ser Gly Ser Gly Thr Asp Phe
                85                  90                  95

Thr Leu Lys Ile Ser Arg Val Glu Ala Glu Asp Val Gly Val Tyr Phe
            100                 105                 110

Cys Phe Gln Gly Ser His Val Pro Phe Thr Phe Gly Gln Gly Thr Lys
        115                 120                 125

Leu Glu Ile Lys
    130

<210> SEQ ID NO 18
<211> LENGTH: 396
<212> TYPE: DNA
<213> ORGANISM: Artificial
<220> FEATURE:
<223> OTHER INFORMATION: 948.g1 VL with signal sequence

<400> SEQUENCE: 18
atgagcgtcc caacacaagt tcttgggctc cttctgctct ggcttactga tgcaagatgc     60
gacgtgctga tgacccagac accctgtca cttagcgtga ctcctggcca acctgcctca    120
atttcctgtc gctccggtca gaatatcgtg cactctaacg gaacaccta cttggagtgg    180 tatctccaaa agcctggcca gagcccaaag ctgctgatct acaaggtctc caatcggttc    240
tttggcgtgc ctgacagaat tagtggtagc ggatccggaa ctgacttcac cctgaaaatc    300
tcacgggtgg aagctgaaga tgtcggcgtg tatttctgct tccaaggctc ccacgttccc    360
tttacgtttg acagggcac caaactggag ataaag                               396

<210> SEQ ID NO 19
<211> LENGTH: 219
<212> TYPE: PRT
<213> ORGANISM: Artificial
<220> FEATURE:
<223> OTHER INFORMATION: 948.g1 light chain (V + constant)

<400> SEQUENCE: 19

Asp Val Leu Met Thr Gln Thr Pro Leu Ser Leu Ser Val Thr Pro Gly
1               5                   10                  15

Gln Pro Ala Ser Ile Ser Cys Arg Ser Gly Gln Asn Ile Val His Ser
            20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Phe Gly Val Pro
 50                  55                  60

Asp Arg Ile Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Phe Gln Gly
                 85                  90                  95

Ser His Val Pro Phe Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 20
<211> LENGTH: 657
<212> TYPE: DNA
<213> ORGANISM: Artificial
<220> FEATURE:
<223> OTHER INFORMATION: 948.g1 light chain (V + constant)

<400> SEQUENCE: 20
gacgtgctga tgacccagac accoctgtca cttagcgtga ctcctggcca acctgcctca      60
atttcctgtc gctccggtca gaatatcgtg cactctaacg ggaacaccta cttggagtgg     120
tatctccaaa agcctggcca gagcccaaag ctgctgatct acaaggtctc caatcggttc     180
tttggcgtgc ctgacagaat tagtggtagc ggatccggaa ctgacttcac cctgaaaatc     240
tcacgggtgg aagctgaaga tgtcggcgtg tatttctgct tccaaggctc ccacgttccc     300
tttacgtttg gacagggcac caaactggag ataaagcgta cggtagcggc ccatctgtc     360 ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt        657

<210> SEQ ID NO 21
<211> LENGTH: 239
<212> TYPE: PRT
<213> ORGANISM: Artificial
<220> FEATURE:
<223> OTHER INFORMATION: 948.g1 light chain with signal sequence

<400> SEQUENCE: 21
```

```
Met Ser Val Pro Thr Gln Val Leu Gly Leu Leu Leu Trp Leu Thr
1               5                   10                  15

Asp Ala Arg Cys Asp Val Leu Met Thr Gln Thr Pro Leu Ser Leu Ser
            20                  25                  30

Val Thr Pro Gly Gln Pro Ala Ser Ile Ser Cys Arg Ser Gly Gln Asn
        35                  40                  45

Ile Val His Ser Asn Gly Asn Thr Tyr Leu Glu Trp Tyr Leu Gln Lys
    50                  55                  60

Pro Gly Gln Ser Pro Lys Leu Leu Ile Tyr Lys Val Ser Asn Arg Phe
65                  70                  75                  80

Phe Gly Val Pro Asp Arg Ile Ser Gly Ser Gly Ser Gly Thr Asp Phe
                85                  90                  95

Thr Leu Lys Ile Ser Arg Val Glu Ala Glu Asp Val Gly Val Tyr Phe
            100                 105                 110

Cys Phe Gln Gly Ser His Val Pro Phe Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 22
<211> LENGTH: 717
<212> TYPE: DNA
<213> ORGANISM: Artificial
<220> FEATURE:
<223> OTHER INFORMATION: 948.g1 light chain with signal sequence

<400> SEQUENCE: 22
atgagcgtcc caacacaagt tcttgggctc cttctgctct ggcttactga tgcaagatgc      60
gacgtgctga tgacccagac cccctgtca cttagcgtga ctcctggcca acctgcctca     120
atttcctgtc gctccggtca gaatatcgtg cactctaacg gaacaccta cttggagtgg     180
tatctccaaa agcctggcca gagcccaaag ctgctgatct acaaggtctc caatcggttc     240
tttggcgtgc ctgacagaat tagtggtagc ggatccggaa ctgacttcac cctgaaaatc     300
tcacgggtgg aagctgaaga tgtcggcgta tatttctgct tccaaggctc cacgttccc     360
tttacgtttg acagggcac caaactggag ataaagcgta cggtagcggc cccatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgt       717
```

<210> SEQ ID NO 23
<211> LENGTH: 119
<212> TYPE: PRT
<213> ORGANISM: Artificial
<220> FEATURE:
<223> OTHER INFORMATION: 948.g1 VH

<400> SEQUENCE: 23

Glu Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
            20                  25                  30

Tyr Ala Trp Asn Trp Ile Arg Gln Pro Pro Gly Lys Lys Leu Glu Trp
        35                  40                  45

Met Gly Tyr Ile Asn Tyr Ser Gly Ser Thr Ser Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Ile Gly Ser Ser Ala Trp Tyr Phe Asp Val Trp Gly Gln
            100                 105                 110

Gly Thr Leu Val Thr Val Ser
        115

<210> SEQ ID NO 24
<211> LENGTH: 357
<212> TYPE: DNA
<213> ORGANISM: Artificial
<220> FEATURE:
<223> OTHER INFORMATION: 948.g1 VH

<400> SEQUENCE: 24
gaagttcagc tgcaagaatc cggccctgga ctcgtgaaac caagccagac actgagcctg        60
acttgcaccg tcactggcta tagcatcacc agcgattacg cctggaactg gataaggcag       120
ccacctggaa agaagctgga gtggatgggc tacatcaact actccggaag cacgtcctac       180
aatccctcac ttaagagcag agtcacaatc tcacgagaca cctccaagaa ccagttctcc       240
ctgaaactga gctccgttac tgccgctgat actgccgtgt actattgtgc aaggtggatt       300
gggagctcag cttggtattt cgacgtttgg ggacaaggca cacttgtgac cgtctcg         357

<210> SEQ ID NO 25
<211> LENGTH: 138
<212> TYPE: PRT
<213> ORGANISM: Artificial
<220> FEATURE:
<223> OTHER INFORMATION: 948.g1 VH with signal sequence

<400> SEQUENCE: 25

Met Glu Trp Ser Trp Val Phe Leu Phe Phe Leu Ser Val Thr Thr Gly
1               5                   10                  15

Val His Ser Glu Val Gln Leu Gln Glu Ser Gly Pro Gly Leu Val Lys
            20                  25                  30

Pro Ser Gln Thr Leu Ser Leu Thr Cys Thr Val Thr Gly Tyr Ser Ile
        35                  40                  45

Thr Ser Asp Tyr Ala Trp Asn Trp Ile Arg Gln Pro Pro Gly Lys Lys
    50                  55                  60

Leu Glu Trp Met Gly Tyr Ile Asn Tyr Ser Gly Ser Thr Ser Tyr Asn

```
                65                  70                  75                  80
Pro Ser Leu Lys Ser Arg Val Thr Ile Ser Arg Asp Thr Ser Lys Asn
                    85                  90                  95

Gln Phe Ser Leu Lys Leu Ser Ser Val Thr Ala Ala Asp Thr Ala Val
                    100                 105                 110

Tyr Tyr Cys Ala Arg Trp Ile Gly Ser Ser Ala Trp Tyr Phe Asp Val
                    115                 120                 125

Trp Gly Gln Gly Thr Leu Val Thr Val Ser
                    130                 135

<210> SEQ ID NO 26
<211> LENGTH: 414
<212> TYPE: DNA
<213> ORGANISM: Artificial
<220> FEATURE:
<223> OTHER INFORMATION: 948.g1 VH with signal sequence

<400> SEQUENCE: 26
atggagtgga gctgggtctt tctcttcttt ctctccgtga ctaccggtgt gcactccgaa     60
gttcagctgc aagaatccgg ccctggactc gtgaaaccaa gccagacact gagcctgact    120
tgcaccgtca ctggctatag catcaccagc gattacgcct ggaactggat aaggcagcca    180
cctggaaaga agctggagtg gatgggctac atcaactact ccggaagcac gtcctacaat    240
ccctcactta agagcagagt cacaatctca cgagacacct ccaagaacca gttctccctg    300
aaactgagct ccgttactgc cgctgatact gccgtgtact attgtgcaag gtggattggg    360
agctcagctt ggtatttcga cgtttgggga caaggcacac ttgtgaccgt ctcg          414

<210> SEQ ID NO 27
<211> LENGTH: 447
<212> TYPE: PRT
<213> ORGANISM: Artificial
<220> FEATURE:
<223> OTHER INFORMATION: 948.g1 heavy chain (V + constant - hu IgG4P)

<400> SEQUENCE: 27

Glu Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
                20                  25                  30

Tyr Ala Trp Asn Trp Ile Arg Gln Pro Pro Gly Lys Lys Leu Glu Trp
            35                  40                  45

Met Gly Tyr Ile Asn Tyr Ser Gly Ser Thr Ser Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Ile Gly Ser Ser Ala Trp Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

165                 170                 175
Leu Gln Ser Ser Gly Leu Tyr Ser Leu Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 28
<211> LENGTH: 1948
<212> TYPE: DNA
<213> ORGANISM: Artificial
<220> FEATURE:
<223> OTHER INFORMATION: 948.g1 heavy chain (V + constant - hu IgG4P)

<400> SEQUENCE: 28
gaagttcagc tgcaagaatc cggccctgga ctcgtgaaac caagccagac actgagcctg      60
acttgcaccg tcactggcta tagcatcacc agcgattacg cctggaactg gataaggcag     120
ccacctggaa agaagctgga gtggatgggc tacatcaact actccggaag cacgtcctac     180
aatccctcac ttaagagcag agtcacaatc tcacgagaca cctccaagaa ccagttctcc     240
ctgaaactga gctccgttac tgccgctgat actgccgtgt actattgtgc aaggtggatt     300
gggagctcag cttggtattt cgacgtttgg ggacaaggca cacttgtgac cgtctcgagc     360
gcttctacaa aggccccatc cgtcttcccc ctggcgccct gctccaggag cacctccgag     420
agcacagccg ccctgggctg cctggtcaag gactacttcc ccgaaccggt gacggtgtcg     480

| | |
|---|---|
| tggaactcag gcgccctgac cagcggcgtg cacaccttcc cggctgtcct acagtcctca | 540 |
| ggactctact ccctcagcag cgtggtgacc gtgccctcca gcagcttggg cacgaagacc | 600 |
| tacacctgca acgtagatca caagcccagc aacaccaagg tggacaagag agttggtgag | 660 |
| aggcagcac agggagggag ggtgtctgct ggaagccagg ctcagccctc ctgcctggac | 720 |
| gcacccgcc tgtgcagccc cagcccaggg cagcaaggca tgccccatct gtctcctcac | 780 |
| ccggaggcct ctgaccaccc cactcatgcc caggagagg gtcttctgga tttttccacc | 840 |
| aggctccggg cagccacagg ctggatgccc ctaccccagg ccctgcgcat acaggggcag | 900 |
| gtgctgcgct cagacctgcc aagagccata tccgggagga ccctgcccct gacctaagcc | 960 |
| caccccaaag gccaaactct ccactccctc agctcagaca ccttctctcc tcccagatct | 1020 |
| gagtaactcc caatcttctc tctgcagagt ccaaatatgg tccccatgc ccaccatgcc | 1080 |
| caggtaagcc aacccaggcc tcgccctcca gctcaaggcg ggacaggtgc cctagagtag | 1140 |
| cctgcatcca gggacaggcc ccagccgggt gctgacgcat ccacctccat ctcttcctca | 1200 |
| gcacctgagt tcctgggggg accatcagtc ttcctgttcc cccaaaacc caaggacact | 1260 |
| ctcatgatct cccggacccc tgaggtcacg tgcgtggtgg tggacgtgag ccaggaagac | 1320 |
| cccgaggtcc agttcaactg gtacgtggat ggcgtggagg tgcataatgc caagacaaag | 1380 |
| ccgcgggagg agcagttcaa cagcacgtac cgtgtggtca gcgtcctcac cgtcctgcac | 1440 |
| caggactggc tgaacggcaa ggagtacaag tgcaaggtct ccaacaaagg cctcccgtcc | 1500 |
| tccatcgaga aaaccatctc caaagccaaa ggtgggaccc acggggtgcg agggccacat | 1560 |
| ggacagaggt cagctcggcc caccctctgc cctgggagtg accgctgtgc caacctctgt | 1620 |
| ccctacaggg cagccccgag agccacaggt gtacaccctg cccccatccc aggaggagat | 1680 |
| gaccaagaac caggtcagcc tgacctgcct ggtcaaaggc ttctacccca gcgacatcgc | 1740 |
| cgtggagtgg gagagcaatg ggcagccgga gaacaactac aagaccacgc ctcccgtgct | 1800 |
| ggactccgac ggctccttct tcctctacag caggctaacc gtggacaaga gcaggtggca | 1860 |
| ggagggaat gtcttctcat gctccgtgat gcatgaggct ctgcacaacc actacacaca | 1920 |
| gaagagcctc tccctgtctc tgggtaaa | 1948 |

<210> SEQ ID NO 29
<211> LENGTH: 466
<212> TYPE: PRT
<213> ORGANISM: Artificial
<220> FEATURE:
<223> OTHER INFORMATION: 948.g1 heavy chain (V + constant - hu IgG4P)
    with signal sequence

<400> SEQUENCE: 29

Met Glu Trp Ser Trp Val Phe Leu Phe Phe Leu Ser Val Thr Thr Gly
1               5                   10                  15

Val His Ser Glu Val Gln Leu Gln Glu Ser Gly Pro Gly Leu Val Lys
            20                  25                  30

Pro Ser Gln Thr Leu Ser Leu Thr Cys Thr Val Thr Gly Tyr Ser Ile
        35                  40                  45

Thr Ser Asp Tyr Ala Trp Asn Trp Ile Arg Gln Pro Pro Gly Lys Lys
    50                  55                  60

Leu Glu Trp Met Gly Tyr Ile Asn Tyr Ser Gly Ser Thr Ser Tyr Asn
65                  70                  75                  80

Pro Ser Leu Lys Ser Arg Val Thr Ile Ser Arg Asp Thr Ser Lys Asn
                85                  90                  95

```
Gln Phe Ser Leu Lys Leu Ser Ser Val Thr Ala Ala Asp Thr Ala Val
                100                 105                 110
Tyr Tyr Cys Ala Arg Trp Ile Gly Ser Ser Ala Trp Tyr Phe Asp Val
            115                 120                 125
Trp Gly Gln Gly Thr Leu Val Thr Val Ser Ser Ala Ser Thr Lys Gly
        130                 135                 140
Pro Ser Val Phe Pro Leu Ala Pro Cys Ser Arg Ser Thr Ser Glu Ser
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
        195                 200                 205
Thr Val Pro Ser Ser Ser Leu Gly Thr Lys Thr Tyr Thr Cys Asn Val
210                 215                 220
Asp His Lys Pro Ser Asn Thr Lys Val Asp Lys Arg Val Glu Ser Lys
225                 230                 235                 240
Tyr Gly Pro Pro Cys Pro Pro Cys Pro Ala Pro Glu Phe Leu Gly Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser Gln Glu
        275                 280                 285
Asp Pro Glu Val Gln Phe Asn Trp Tyr Val Asp Gly Val Glu Val His
290                 295                 300
Asn Ala Lys Thr Lys Pro Arg Glu Glu Gln Phe Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Gly Leu Pro Ser Ser Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Gln Glu Glu Met Thr Lys Asn Gln Val Ser Leu
370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Arg Leu Thr Val Asp
            420                 425                 430
Lys Ser Arg Trp Gln Glu Gly Asn Val Phe Ser Cys Ser Val Met His
        435                 440                 445
Glu Ala Leu His Asn His Tyr Thr Gln Lys Ser Leu Ser Leu Ser Leu
450                 455                 460
Gly Lys
465

<210> SEQ ID NO 30
<211> LENGTH: 2005
<212> TYPE: DNA
<213> ORGANISM: Artificial
<220> FEATURE:
<223> OTHER INFORMATION: 948.g1 heavy chain (V + constant - hu IgG4P)
``` with signal sequence

<400> SEQUENCE: 30

```
atggagtgga gctgggtctt tctcttcttt ctctccgtga ctaccggtgt gcactccgaa      60
gttcagctgc aagaatccgg ccctggactc gtgaaaccaa gccagacact gagcctgact     120
tgcaccgtca ctggctatag catcaccagc gattacgcct ggaactggat aaggcagcca     180
cctggaaaga agctggagtg gatgggctac atcaactact ccggaagcac gtcctacaat     240
ccctcactta agagcagagt cacaatctca cgagacacct ccaagaacca gttctccctg     300
aaactgagct ccgttactgc cgctgatact gccgtgtact attgtgcaag gtggattggg     360
agctcagctt ggtatttcga cgtttgggga caaggcacac ttgtgaccgt ctcgagcgct     420
tctacaaagg gcccatccgt cttccccctg gcgccctgct ccaggagcac ctccgagagc     480
acagccgccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac gaagacctac     660
acctgcaacg tagatcacaa gcccagcaac accaaggtgg acaagagagt tggtgagagg     720
ccagcacagg gagggagggt gtctgctgga agccaggctc agccctcctg cctggacgca     780
ccccggctgt gcagcccag ccagggcag caaggcatgc ccatctgtc tcctcacccg       840
gaggcctctg accaccccac tcatgcccag ggagagggtc ttctggattt ttccaccagg    900
ctccgggcag ccacaggctg gatgccccta ccccaggccc tgcgcataca ggggcaggtg    960
ctgcgctcag acctgccaag agccatatcc gggaggaccc tgcccctgac ctaagcccac   1020
cccaaaggcc aaactctcca ctccctcagc tcagacacct tctctcctcc cagatctgag   1080
taactcccaa tcttctctct gcagagtcca aatatggtcc cccatgccca ccatgccag    1140
gtaagccaac ccaggcctcg ccctccagct caaggcggga caggtgccct agagtagcct   1200
gcatccaggg acaggcccca gccgggtgct gacgcatcca cctccatctc ttcctcagca   1260
cctgagttcc tggggggacc atcagtcttc ctgttccccc caaaacccaa ggacactctc   1320
atgatctccc ggacccctga ggtcacgtgc gtggtggtgg acgtgagcca ggaagacccc   1380
gaggtccagt tcaactggta cgtggatggc gtggaggtgc ataatgccaa gacaaagccg   1440
cgggaggagc agttcaacag cacgtaccgt gtggtcagcg tcctcaccgt cctgcaccag   1500
gactggctga acggcaagga gtacaagtgc aaggtctcca acaaaggcct cccgtcctcc   1560
atcgagaaaa ccatctccaa agccaaaggt gggacccacg gggtgcgagg gccacatgga   1620
cagaggtcag ctcggcccac cctctgccct gggagtgacc gctgtgccaa cctctgtccc   1680
tacagggcag ccccgagagc cacaggtgta ccctgcccc catcccagg aggagatgac     1740
caagaaccag gtcagcctga cctgcctggt caaaggcttc taccccagcg acatcgccgt   1800
ggagtgggag agcaatgggc agccggagaa caactacaag accacgcctc ccgtgctgga   1860
ctccgacggc tccttcttcc tctacagcag gctaaccgtg gacaagagca ggtggcagga   1920
ggggaatgtc ttctcatgct ccgtgatgca tgaggctctg cacaaccact acacacagaa   1980
gagcctctcc ctgtctctgg gtaaa                                         2005
```

<210> SEQ ID NO 31
<211> LENGTH: 112
<212> TYPE: PRT
<213> ORGANISM: Artificial
<220> FEATURE:
<223> OTHER INFORMATION: Human VK2 4-1-(1) A18 JK2 acceptor framework

<400> SEQUENCE: 31

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro Tyr Thr Phe Gly Gln Gly Thr Lys Leu Glu Ile Lys
            100                 105                 110

<210> SEQ ID NO 32
<211> LENGTH: 336
<212> TYPE: DNA
<213> ORGANISM: Artificial
<220> FEATURE:
<223> OTHER INFORMATION: Human VK2 4-1-(1) A18 JK2 acceptor framework

<400> SEQUENCE: 32
gatattgtga tgacccagac tccactctct ctgtccgtca cccctggaca gccggcctcc      60
atctcctgca gtctagtca gagcctcctg catagtgatg aaagaccta tttgtattgg      120 tacctgcaga agccaggcca gtctccacag ctcctaatct atgaagtttc cagccggttc    180
tctggagtgc cagataggtt cagtggcagc gggtcaggga cagatttcac actgaaaatc    240
agccgggtgg aggctgagga tgttggggtt tattactgca tgcaaggtat acaccttcct    300
tacacttttg gccagggac caagctggag atcaaa                              336

<210> SEQ ID NO 33
<211> LENGTH: 113
<212> TYPE: PRT
<213> ORGANISM: Artificial
<220> FEATURE:
<223> OTHER INFORMATION: Human VH4 3-1 4-30.4 JH4 acceptor framework

<400> SEQUENCE: 33

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Tyr Phe Asp Tyr Trp Gly Gln Gly Thr Leu Val Thr Val
            100                 105                 110

Ser

```
<210> SEQ ID NO 34
<211> LENGTH: 339
<212> TYPE: DNA
<213> ORGANISM: Artificial
<220> FEATURE:
<223> OTHER INFORMATION: Human VH4 3-1 4-30.4 JH4 acceptor framework

<400> SEQUENCE: 34
caggtgcagc tgcaggagtc gggcccagga ctggtgaagc cttcacagac cctgtccctc         60
acctgcactg tctctggtgg ctccatcagc agtggtgatt actactggag ttggatccgc        120
cagcccccag ggaagggcct ggagtggatt gggtacatct attacagtgg gagcacctac        180
tacaacccgt ccctcaagag tcgagttacc atatcagtag acacgtccaa gaaccagttc        240
tccctgaagc tgagctctgt gactgccgca gacacggccg tgtattactg tgccagatac        300
tttgactact ggggccaggg aaccctggtc accgtctcc                               339

<210> SEQ ID NO 35
<211> LENGTH: 14
<212> TYPE: PRT
<213> ORGANISM: Artificial
<220> FEATURE:
<223> OTHER INFORMATION: human JH4

<400> SEQUENCE: 35

Tyr Phe Asp Tyr Trp Gly Gln Gly Thr Leu Val Thr Val Ser
1               5                   10

<210> SEQ ID NO 36
<211> LENGTH: 12
<212> TYPE: PRT
<213> ORGANISM: Artificial
<220> FEATURE:
<223> OTHER INFORMATION: JK2 sequence

<400> SEQUENCE: 36

Tyr Thr Phe Gly Gln Gly Thr Lys Leu Glu Ile Lys
1               5                   10
```

PD-1 ANTIBODY

The present invention relates to antibody molecules having specificity for antigenic determinants of human PD-1 and compositions comprising the same. The present invention also relates to the therapeutic uses of the antibody molecules, compositions and methods for producing said antibody molecules.

Programmed Death 1 (PD-1), also known as CD279; gene name PDCD1; accession number NP_005009 is a cell surface receptor with a critical role in regulating the balance between stimulatory and inhibitory signals in the immune system and maintaining peripheral tolerance (Ishida, Y et al. 1992 EMBO J. 11 3887; Kier, Mary E et al. 2008 Annu Rev Immunol 26 677-704; Okazaki, Taku et al. 2007 International Immunology 19 813-824). It is an inhibitory member of the immunoglobulin super-family with homology to CD28. The structure of PD-1 is a monomeric type 1 transmembrane protein, consisting of one immunoglobulin variable-like extracellular domain and a cytoplasmic domain containing an immunoreceptor tyrosine-based inhibitory motif (ITIM) and an immunoreceptor tyrosine-based switch motif (ITSM). Expression of PD-1 is inducible on T cells, B cells, natural killer (NK) cells and monocytes, for example upon lymphocyte activation via T cell receptor (TCR) or B cell receptor (BCR) signalling (Kier, Mary E et al. 2008 Annu Rev Immunol 26 677-704; Agata, Y et al 1996 Int Immunol 8 765-72). PD-1 has two known ligands, PD-L1 (B7-H1, CD274) and PD-L2 (B7-DC, CD273), which are cell surface expressed members of the B7 family (Freeman, Gordon et al. 2000 J Exp Med 192 1027; Latchman, Y et al. 2001 Nat Immunol 2 261). Upon ligand engagement, PD-1 recruits phosphatases such as SHP-1 and SHP-2 to its intracellular tyrosine motifs which subsequently dephosphorylate effector molecules activated by TCR or BCR signalling (Chemnitz, J et al. 2004 J Immunol 173 945-954; Riley, James L 2009 Immunological Reviews 229 114-125) In this way, PD-1 transduces inhibitory signals into T and B cells only when it is engaged simultaneously with the TCR or BCR.

PD-1 has been demonstrated to down-regulate effector T cell responses via both cell-intrinsic and cell-extrinsic functional mechanisms. Inhibitory signalling through PD-1 induces a state of anergy or unresponsiveness in T cells, resulting in the cells being unable to clonally expand or produce optimal levels of effector cytokines. PD-1 may also induce apoptosis in T cells via its ability to inhibit survival signals from co-stimulation, which leads to reduced expression of key anti-apoptotic molecules such as $Bcl_{-xL}$ (Kier, Mary E et al. 2008 Annu Rev Immunol 26 677-704). In addition to these direct effects, recent publications have implicated PD-1 as being involved in the suppression of effector cells by promoting the induction and maintenance of regulatory T cells ($T_{REG}$). For example, PD-L1 expressed on dendritic cells was shown to act in synergy with TGF-β to promote the induction of $CD4^+$ $FoxP3^+T_{REG}$ with enhanced suppressor function (Francisco, Loise M et al. 2009 J Exp Med 206 3015-3029).

The first indication of the importance of PD-1 in peripheral tolerance and inflammatory disease came from the observation that PD-1 knockout ($Pdcd1^{-/-}$) mice develop spontaneous autoimmunity. Fifty percent of $Pdcd1^{-/-}$ mice on a C57BL/6 background develop lupus-like glomerulonephritis and arthritis by 14 months of age and BALB/c-$Pdcd1^{-/-}$ mice develop a fatal dilated cardiomyopathy and production of autoantibodies against cardiac troponin I from 5 weeks onwards (Nishimura, H et al. 1999 Immunity 11 141-151; Nishimura, H et al. 2001 Science 291 319-322). Furthermore, introduction of PD-1 deficiency to the non-obese diabetic (NOD) mouse strain dramatically accelerates the onset and incidence of diabetes resulting in all NOD-$Pdcd1^{-/-}$ mice developing diabetes by 10 weeks of age (Wang, J et al. 2005 Proc Natl Acad Sci USA 102 11823). Additionally, using induced murine models of autoimmunity such as experimental autoimmune encephalomyelitis (EAE), or transplantation/graft-versus-host (GVHD) models, several groups have shown that blocking the PD-1-PD-L interaction exacerbates disease, further confirming the key role of PD-1 in inflammatory diseases. Importantly, evidence suggests that PD-1 has a comparable immune modulatory function in humans as mice, as polymorphisms in human PDCD1 have been associated with a range of autoimmune diseases including systemic lupus erythematosus (SLE), multiple sclerosis (MS), type I diabetes (TID), rheumatoid arthritis (RA) and Grave's disease (Okazaki, Taku et al. 2007 International Immunology 19 813-824; Prokunina, L et al. 2002 Nat Genet. 32 666-669; Kroner, A et al. 2005 Ann Neurol 58 50-57; Prokunina, L et al 2004 Arthritis Rheum 50 1770). Several therapeutic approaches to enhance PD-1 signalling and modulate inflammatory disease have been reported, using murine models of autoimmunity. One such approach tried was to generate artificial dendritic cells which over-express PD-L1. Injection of mice with antigen-loaded PD-L1-dendritic cells before or after induction of EAE by MOG peptide immunisation reduced the inflammation of the spinal cord as well as the clinical severity of the disease (Hirata, S et al. 2005 J Immunol 174 1888-1897). Another approach was to try and cure lupus-like syndrome in BXSB mice by delivering a PD-1 signal using a recombinant adenovirus expressing mouse PD-L1. Injection of this virus partially prevented the development of nephritis as shown by lower frequency of protinuria, reduced serum anti-dsDNA Ig and better renal pathology (Ding, H et al. 2006 Clin Immunol 118 258). These results suggest that enhancing the PD-1 signal could have therapeutic benefit in human autoimmune disease. An alternative therapeutic approach more appropriate as a human drug treatment would be to use an agonistic monoclonal antibody against human PD-1. Such an antibody may work as a 'ligand mimic' by binding to the ligand binding site of PD-1 and thereby inducing an inhibitory signalling cascade in the same way that engagement of the endogenous PD-1 ligands do. An agonistic anti-PD-1 mAb would be predicted to modulate a range of immune cell types involved in inflammatory disease including T cells, B cells, NK cells and monocytes and would therefore have utility in the treatment of a wide range of human autoimmune or inflammatory disorders.

A number of antagonistic anti-PD-1 antibodies have been described, and some agonistic antibodies see for Example, WO2004/056875.

There is still a need in the art for improved agonistic anti-PD-1 antibodies suitable for treating patients.

We have now identified high affinity agonistic anti-PD-1 antibodies suitable for use in the treatment or prophylaxis of immune disorders, for example by reducing the T cell response. Non limiting examples of immune disorders that can be treated via the administration of PD-1 specific antibodies to a subject include, but are not limited to, rheumatoid arthritis, multiple sclerosis, inflammatory bowel disease, Crohn's disease, systemic lupus erythematosus, type I diabetes, transplant rejection, graft-versus-host disease, hyperproliferative immune disorders, cancer and infectious diseases.

BRIEF DESCRIPTION OF THE DRAWINGS

FIGS. 1-3 shows amino acid sequences relating to antibody 948 according to the disclosure FIGS. 3-11 shows certain amino acid or DNA sequences relating to an antibody according to the disclosure FIG. 12 Comparison of 948 chimeric and humanised grafts binding to cell expressed human PD-1

FIG. 13 shows an alignment of the light and heavy chains for the murine, acceptor frameworks and humanised light and heavy chains.

Figure 12:
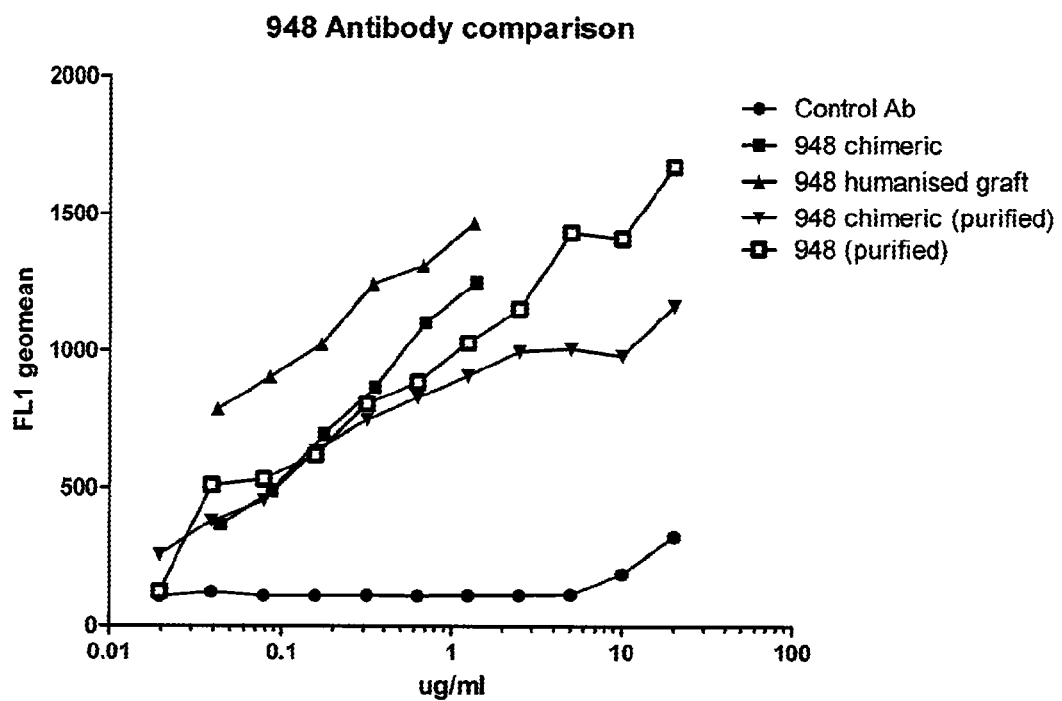

The parental murine antibody hybridoma from which the humanised antibodies are derived is referred to herein as Clone 10. The cloned recombinant antibody derived from Clone 10 is referred to herein as antibody CA05100948 also referred to herein as 948.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

As used herein, the term 'agonistic antibody' describes an antibody that is capable of stimulating the biological signalling activity of PD-1, leading to phosphatase recruitment to its intracellular domain and hence inactivation of T or B cell receptor signaling and phenotypic characteristics associated with activation.

Antibodies for use in the present invention may be obtained using any suitable method known in the art. The PD-1 polypeptide/protein including fusion proteins, for example PD-1-Fc fusions proteins or cells (recombinantly or naturally) expressing the polypeptide (such as activated T cells) can be used to produce antibodies which specifically recognise PD-1. The PD-1 polypeptide may be the 'mature' polypeptide or a biologically active fragment or derivative thereof. Suitably the PD-1 polypeptide is the mature human polypeptide or the extracellular domain or fragment thereof. The extracellular domain typically comprises amino acids 21-170 of the PD-1 protein (SWISS PROT entry Q15116). PD-1 polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The PD-1 polypeptide may in some instances be part of a larger protein such as a fusion protein for example fused to an affinity tag. Antibodies generated against the PD-1 polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15): 7843-78481; WO92/02551; WO2004/051268 and International Patent Application number WO2004/106377.

Screening for antibodies can be performed using assays to measure binding to human PD-1 and/or assays to measure the ability to agonise PD1 activity. An example of a binding assay is an ELISA, in particular, using a fusion protein of human PD-1 and human Fc, which is immobilized on plates, and employing a conjungated secondary antibody to detect anti-PD-1 antibody bound to the fusion protein.

Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

The present invention provides agonistic humanised antibodies having specificity for human PD-1.

An agonistic murine anti-PD-1 antibody (Clone 10) was described in PCT/IB2009/06946 (unpublished) and the sequences of the variable regions and CDRs of this antibody are provided in FIGS. 1 and 2. In particular the CDRs of this antibody are provided in FIG. 1, SEQ ID NOs 1-6.

As used herein, the term 'humanised antibody molecule' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the humanised antibody according to the present invention has a variable domain comprising human acceptor framework regions as well as one or more of the CDRs provided in FIG. 1 (SEQ ID Nos 1-6). Thus, provided in one embodiment is an agonistic humanised antibody which binds human PD-1 wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-cpe.cam.ac.uk/

In a humanised antibody of the present invention, the acceptor heavy and light chains do not necessarily need to be derived from the same antibody and may, if desired, comprise composite chains having framework regions derived from different chains.

Once such suitable framework region for the heavy chain of the humanised antibody of the present invention is derived from the human sub-group VH4 sequence 3-1 4-30.4 together with JH4 (SEQ ID NO:33). Accordingly, in one example there is provided an agonistic humanised antibody comprising the sequence given in SEQ ID NO:1 for CDR-H1, the sequence given in SEQ ID NO:2 for CDR-H2 and the sequence given in SEQ ID NO:3 for CDRH3 wherein the heavy chain framework region is derived from the human subgroup VH4 sequence 3-1 4-30.4 together with JH4. The sequence of human JH4 is as follows: (YFDY) WGQGTLVTVS (Seq ID No: 35). The YFDY motif is part of CDR-H3 and is not part of framework 4 (Ravetch, J V. et al., 1981, *Cell*, 27, 583-591).

A suitable framework region for the light chain of the humanised antibody of the present invention is derived from the human germline sub-group VK2 sequence 4-1-1 A18 together with JK2 (SEQ ID NO:31). Accordingly, in one example there is provided an agonistic humanised antibody comprising the sequence given in SEQ ID NO:4 for CDR-L1, the sequence given in SEQ ID NO:5 for CDR-L2 and the sequence given in SEQ ID NO:6 for CDRL3 wherein the light chain framework region is derived from the human subgroup sequence VK2 4-1-1 A18 together with JK2. The JK2 sequence is as follows: (YT)FGQGTKLEIK (Seq ID No: 36). The YT motif is part of CDR-L3 and is not part of framework 4 (Hieter, P A., et al., 1982, J. Biol. Chem., 257, 1516-1522).

Also, in a humanised antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

Suitably, in a humanised antibody molecule of the present invention, if the acceptor heavy chain has the human VH4 sequence 3-1 4-30.4 together with JH4, then the acceptor framework regions of the heavy chain comprise, in addition to the three donor CDRs (SEQ ID NOs:1, 2 and 3), a donor residue at at least one of positions 25, 44, 48 and 71 (according to Kabat et al., (supra)). Accordingly, in one example there is provided a humanised antibody, wherein at least the residues at each of positions 25, 44, 48 and 71 of the variable domain of the heavy chain are donor residues, see for example the sequence given in SEQ ID NO:23.

Suitably, in a humanised antibody molecule according to the present invention, if the acceptor light chain has the human sub-group VK2 sequence 4-1-1 A18 together with JK2, then the acceptor framework regions of the light chain comprise, in addition to three donor CDRs (SEQ ID NOs:4, 5 and 6), a donor residue at at least one of positions 2, 3, 45, 62 and 87. Accordingly, in one example there is provided a humanised antibody, wherein at least the residues at each of positions 2, 3, 45, 62 and 87 of the variable domain of the light chain are donor residues, see for example SEQ ID NO:15.

Donor residues are residues from the donor antibody, i.e. the antibody from which the CDRs were originally derived. Donor residues may be replaced by a suitable residue derived from a human receptor framework (acceptor residues).

Suitable human acceptor residues to replace donor residues for each framework are listed below:

Light Chain

| Kabat position | Human residue to replace donor |
|---|---|
| 2 | Isoleucine |
| 3 | Valine |
| 45 | Glutamine |
| 62 | Phenylalanine |
| 87 | Tyrosine |

Heavy Chain

| Kabat position | Human residue to replace donor |
|---|---|
| 25 | Serine |
| 44 | Glycine |
| 48 | Isoleucine |
| 71 | Valine |

The antibody molecules of the present invention suitably comprise a complementary light chain or a complementary heavy chain, respectively. Accordingly, in one embodiment the present invention provides a humanised agonistic antibody which binds human PD-1 having a heavy chain comprising the sequence given in SEQ ID NO:23 and a light chain comprising the sequence given in SEQ ID NO: 15.

It will be appreciated that one or more amino acid substitutions, additions and/or deletions may be made to the CDRs or other sequences (e.g. variable domains) provided by the present invention without significantly altering the ability of the antibody to bind to PD-1 and to agonise PD-1 activity. The effect of any amino acid substitutions, additions and/or deletions can be readily tested by one skilled in the art, for example by using the methods described herein, in particular in the Examples, to determine PD-1 binding and PD-1 agonism.

In another embodiment, an antibody of the present invention comprises a heavy chain, wherein the variable domain of the heavy chain comprises a sequence having at least 60% identity or similarity to the sequence given in SEQ ID NO:23. In one embodiment, an antibody of the present invention comprises a heavy chain, wherein the variable domain of the heavy chain comprises a sequence having at least 70%, 80%, 90%, 95% or 98% identity or similarity to the sequence given in SEQ ID NO:23.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

In another embodiment, an antibody of the present invention comprises a light chain, wherein the variable domain of the light chain comprises a sequence having at least 60% identity or similarity to the sequence given in SEQ ID NO: 15. In one embodiment the antibody of the present invention comprises a light chain, wherein the variable domain of the light chain comprises a sequence having at least 70%, 80%, 90%, 95% or 98% identity or similarity to the sequence given in SEQ ID NO: 15.

In another embodiment of the invention, the antibody comprises a heavy chain and a light chain, wherein the variable domain of the heavy chain comprises a sequence having at least 60% identity or similarity to the sequence given in SEQ ID NO:23 and the variable domain of the light chain comprises a sequence having at least 60% identity or similarity to the sequence given in SEQ ID NO: 15.

Suitably, the antibody comprises a heavy chain, wherein the variable domain of the heavy chain comprises a sequence having at least 70%, 80%, 90%, 95% or 98% identity or similarity to the sequence given in SEQ ID NO:23 and a light chain, wherein the variable domain of the light chain comprises a sequence having at least 70%, 80%, 90%, 95% or 98% identity or similarity to the sequence given in SEQ ID NO: 15.

The antibody molecules of the present invention may comprise a complete antibody molecule having full length heavy and light chains or a fragment thereof and may be, but are not limited to Fab, modified Fab, Fab', modified Fab', F(ab')$_2$, Fv, single domain antibodies (e.g. VH or VL or VHH), scFv, bi, tri or tetra-valent antibodies, Bis-scFv, diabodies, triabodie tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities e.g. bispecific or may be monospecific (see for example WO 92/22583 and WO05/113605).

In one embodiment the antibody according to the present disclosure is provided as PD-1 binding antibody fusion protein which comprises an immunoglobulin moiety, for example a Fab or Fab' fragment, and one or two single domain antibodies (dAb) linked directly or indirectly thereto, for example as described in WO2009/040562.

In one embodiment the fusion protein comprises two domain antibodies, for example as a variable heavy (VH) and variable light (VL) pairing, optionally linked by a disulphide bond.

In one embodiment the Fab or Fab' element of the fusion protein has the same or similar specificity to the single domain antibody or antibodies. In one embodiment the Fab or Fab' has a different specificity to the single domain antibody or antibodies, that is to say the fusion protein is multivalent. In one embodiment a multivalent fusion protein according to the present invention has an albumin binding site, for example a VH/VL pair therein provides an albumin binding site.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply agonising PD-1 activity. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705:129-134, 1995). Accordingly, the C-terminal lysine of the antibody heavy chain given in FIG. 7, SEQ ID NO: 27 may be absent.

In one embodiment the antibody heavy chain comprises a CH1 domain and the antibody light chain comprises a CL domain, either kappa or lambda.

Examples of suitable sequences comprising constant domains are provided in SEQ ID NOs 19 and 27.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent accessible surface thereof carries no net electrical charge. In one example, the PD-1 antibody and fragments of the invention may be engineered to have an appropriate isoelectric point. This may lead to antibodies and/or fragments with more robust properties, in particular suitable solubility and/or stability profiles and/or improved purification characteristics.

Thus in one aspect the invention provides a humanised PD-1 antibody engineered to have an isoelectric point different to that of the originally identified antibody 948. The antibody may, for example be engineered by replacing an amino acid residue such as replacing an acidic amino acid residue with one or more basic amino acid residues. Alternatively, basic amino acid residues may be introduced or acidic amino acid residues can be removed. Alternatively, if the molecule has an unacceptably high pI value acidic residues may be introduced to lower the pI, as required. It is important that when manipulating the pI care must be taken to retain the desirable activity of the antibody or fragment. Thus in one embodiment the engineered antibody or fragment has the same or substantially the same activity as the "unmodified" antibody or fragment.

Programs such as ** ExPASY http://www.expasy.ch/tools/pi_tool.html, and http://www.iut-arles.up.univ-mrs.fr/w3bb/d_abim/compo-p.html, may be used to predict the isoelectric point of the antibody or fragment.

It will be appreciated that the affinity of antibodies provided by the present invention may be altered using any suitable method known in the art. The affinity of the antibodies or variants thereof may be measured using any suitable method known in the art, including BIAcore, using isolated natural or recombinant PD-1 or a suitable fusion protein/polypeptide. In one example affinity is measured using recombinant human PD-1 extracellular domain. In one example the recombinant human PD-1 extracellular domain used is a monomer. The present invention therefore also relates to variants of the antibody molecules of the present invention, which have an improved affinity for PD-1. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment the antibody molecules of the present invention agonise human PD-1 activity. Assays suitable for determining the ability of an antibody to agonise PD-1 are known in the art.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin. Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment or diFab which is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA2 (wherein m in the structure below is 5) and GL2-400MA (where m is 2) and n is approximately 450:

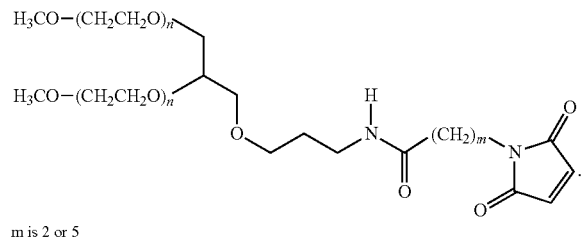

m is 2 or 5

That is to say each PEG is about 20,000 Da.
Further alternative PEG effector molecules of the following type:

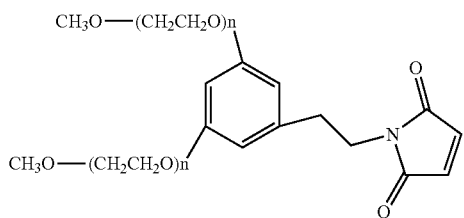

are available from Dr Reddy, NOF and Jenkem.

In one embodiment there is provided an antibody which is PEGylated (for example with a PEG described herein), attached through a cysteine amino acid residue at or about amino acid 226 in the chain, for example amino acid 226 of the heavy chain (by sequential numbering).

The present invention also provides an isolated DNA sequence encoding the heavy and/or light chain(s) of an antibody molecule of the present invention. Suitably, the DNA sequence encodes the heavy or the light chain of an antibody molecule of the present invention. The DNA sequence of the present invention may comprise synthetic DNA, for instance produced by chemical processing, cDNA, genomic DNA or any combination thereof. DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable DNA sequences are provided in FIGS. 3-12, in particular SEQ ID NOs 16, 18, 20, 22, 24, 26, 28 and 30.

The present invention also relates to a cloning or expression vector comprising one or more DNA sequences of the present invention. Accordingly, provided is a cloning or expression vector comprising one or more DNA sequences encoding an antibody of the present invention. Suitably, the cloning or expression vector comprises two DNA sequences, encoding the light chain and the heavy chain of the antibody molecule of the present invention, respectively and suitable signal sequences. In one example the vector comprises an intergenic sequence between the heavy and the light chains (see WO03/048208).

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibodies and fragments according to the present disclosure are expressed at good levels from host cells. Thus the properties of the antibodies and/or fragments are optimised and conducive to commercial processing.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines.

In a further embodiment the antibody, fragment or composition according to the disclosure is employed in combination with a further pharmaceutically active agent, for example a corticosteroid (such as fluticasonoe propionate) and/or a beta-2-agonist (such as salbutamol, salmeterol or formoterol) or inhibitors of cell growth and proliferation (such as rapamycin, cyclophosphmide, methotrexate) or alternative a CD28 and/or CD40 inhibitor. In one embodiment the inhibitor is a small molecule. In another embodiment the inhibitor is an antibody specific to the target.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, for example 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody or fragment, for example if the pH of the formulation is 7 then a pI of from 8-9 or above may be appropriate. Whilst not wishing to be bound by theory it is thought that this may ultimately provide a final formulation with improved stability, for example the antibody or fragment remains in solution.

In one embodiment the pharmaceutical formulation at a pH in the range of 4.0 to 7.0 comprises: 1 to 200 mg/mL of an antibody according to the present disclosure, 1 to 100 mM of a buffer, 0.001 to 1% of a surfactant, a) 10 to 500 mM of a stabiliser, b) 10 to 500 mM of a stabiliser and 5 to 500 mM of a tonicity agent, or c) 5 to 500 mM of a tonicity agent.

For example the formulation at approximately pH6 may comprise 1 to 50 mg/mL of antibody, 20 mM L-histidine HCl, 240 mM trehalose and 0.02% polysorbate 20. Alternatively a formulation at approximately pH 5.5 may comprise 1 to 50 mg/mL of antibody, 20 mM citrate buffer, 240 mM sucrose, 20 mM arginine, and 0.02% polysorbate 20.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the above-mentioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 µm, in particular from 1 to 5 µm. The particle size of the active ingredient (such as the antibody or fragment) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoro ethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus(R) nebulizer connected to a Pari Master(R) compressor manufactured by Pari Respiratory Equipment, Inc., Richmond, Va.).

The antibody of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The antibodies disclosed herein may be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody molecule (or compositions comprising same) for use in the control of inflammatory diseases, for example acute or chronic inflammatory disease. Suitably, the antibody molecule (or compositions comprising same) can be used to reduce the inflammatory process or to prevent the inflammatory process. In one embodiment there is provided an in vivo reduction of activated T cells, in particular those involved in inappropriate inflammatory immune responses, for example recruited to the vicinity/location of such a response.

Reduction of activated T cells, as employed herein, may be a reduction, 10, 20, 30, 40, 50, 60, 70, 80, 90 or more percent in comparison to before treatment or without treatment. Advantageously, treatment with an antibody, fragment or composition according to the present invention, may allow the reduction in the level of activated T cells, without reducing the patients general level of T cells (unactivated T cells). This may result in fewer side effects, and possibly prevent T cell depletion in the patient.

The present invention also provides the antibody molecule of the present invention for use in the treatment or prophylaxis of an immune disorder. The immune disorder, may, for example be selected from the group consisting of infections (viral, bacterial, fungal and parasitic), endotoxic shock associated with infection, arthritis, rheumatoid arthritis, asthma, COPD, pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis and hypochlorhydia or infertility related to loss of fetal-maternal tolerance.

In one embodiment the antibody according to the invention is employed in the treatment of allergy, COPD, autoimmune disease or rheumatoid arthritis.

The present invention also provides an antibody molecule according to the present invention for use in the treatment or prophylaxis of pain, particularly pain associated with inflammation.

The present invention further provides the use of an antibody molecule, fragment or composition according to the present invention in the manufacture of a medicament for the treatment or prophylaxis of an immune disorder, in particular the immune disorder is rheumatoid arthritis, asthma or COPD.

The present invention further provides the use of an antibody molecule, fragment or composition according to the present invention in the manufacture of a medicament for the treatment or prophylaxis of one or more medical indications described herein.

An antibody molecule, fragment or composition of the present invention may be utilised in any therapy where it is desired to increase the effects of PD-1 in the human or animal body.

In one embodiment the antibody molecule of the present invention or a composition comprising the same is used for the control of inflammatory disease, e.g. as described herein.

The present invention also provides a method of treating human or animal subjects suffering from or at risk of an immune disorder, the method comprising administering to the subject an effective amount of the antibody molecule of the present invention, or a composition comprising the same.

In one embodiment there is provided a process for purifying an antibody (in particular an antibody or fragment according to the invention) comprising the steps: performing anion exchange chromatography in non-binding mode such that the impurities are retained on the column and the antibody is eluted.

Suitable ion exchange resins for use in the process include Q.FF resin (supplied by GE-Healthcare). The step may, for example be performed at a pH about 8.

The process may further comprise an initial capture step employing cation exchange chromatography, performed for example at a pH of about 4 to 5, such as 4.5. The cation exchange chromatography may, for example employ a resin such as CaptoS resin or SP sepharose FF (supplied by GE-Healthcare). The antibody or fragment can then be eluted from the resin employing an ionic salt solution such as sodium chloride, for example at a concentration of 200 mM.

Thus the chromatograph step or steps may include one or more washing steps, as appropriate.

The purification process may also comprise one or more filtration steps, such as a dia filtration step.

Thus in one embodiment there is provided a purified anti-PD-1 antibody or fragment, for example a humanised antibody or fragment, in particular an antibody or fragment according to the invention, in substantially purified from, in particular free or substantially free of endotoxin and/or host cell protein or DNA.

Purified form as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 µg per mg of antibody product or less such as 100 µg per mg or less, in particular 20 µg per mg, as appropriate.

The antibody molecule of the present invention may also be used in diagnosis, for example in the in vivo diagnosis and imaging of disease states involving PD-1.

Comprising in the context of the present specification is intended to meaning including.

Where technically appropriate embodiments of the invention may be combined.

Embodiments are described herein as comprising certain features/elements. The disclosure also extends to separate embodiments consisting or consisting essentially of said features/elements.

The present invention is further described by way of illustration only in the following examples, which refer to the accompanying Figures, in which:

FIG. 1 in detail:
CDRH1 (SEQ ID NO:1), CDRH2 (SEQ ID NO:2), CDRH3 (SEQ ID NO:3), CDRL1 (SEQ ID NO:4), CDRL2 (SEQ ID NO:5), CDRL3 (SEQ ID NO:6) of antibody 948
Light chain V region of antibody 948 (SEQ ID NO:7)
Light chain V region DNA of antibody 948 (SEQ ID NO:8)
Light chain V region with signal sequence of antibody 948 (SEQ ID NO:9)
FIG. 2
Light chain V region DNA with signal sequence of antibody 948 (SEQ ID NO:10)
Mouse Ab948 VH region (SEQ ID NO:11)
Mouse Ab948 VH region DNA (SEQ ID NO:12)
Mouse Ab948 VH region with signal sequence (SEQ ID NO:13)
FIG. 3
Mouse Ab948 VH region DNA with signal sequence (SEQ ID NO:14)
948 VL gL1 V region (SEQ ID NO:15)
948 VL gL1 V region DNA (SEQ ID NO:16)
948 VL gL1 V region with signal sequence (SEQ ID NO:17)
FIG. 4
948 VL gL1 V region DNA with signal sequence (SEQ ID NO:18)
948 VL gL1 light chain V+constant (SEQ ID NO:19)
FIG. 5
948 VL gL1 light chain V+constant DNA (SEQ ID NO:20)
948 VL gL1 light chain V+constant with signal sequence (SEQ ID NO:21)

FIG. 6
948 VL gL1 light chain V+constant with signal sequence (SEQ ID NO:22)
948 VH g1 (SEQ ID NO:23)
948 VH g1 DNA (SEQ ID NO:24)
FIG. 7
948 VH g1 with signal sequence (SEQ ID NO:25)
948 VH g1 with signal sequence DNA (SEQ ID NO:26)
948 VH g1 and constant domain (SEQ ID NO:27)
FIG. 8
948 VH g1 and constant domain DNA (SEQ ID NO:28)
FIG. 9
948 VH g1 and constant domain and signal sequence (SEQ ID NO:29)
FIG. 10
948 VH g1 and constant domain and signal sequence DNA (SEQ ID NO:30)
FIG. 11
Human VK2 4-1-(1) A18 JK2 acceptor framework (SEQ ID NO:31)
Human VK2 4-1-(1) A18 JK2 acceptor framework DNA (SEQ ID NO:32)
Human VH4 3-1 4-30.4 JH4 acceptor framework (SEQ ID NO:33)
Human VH4 3-1 4-30.4 JH4 acceptor framework (SEQ ID NO:34)
FIG. 12 Comparison of 948 chimeric and humanised grafts binding to cell expressed human PD-1. Binding of the indicated concentrations of 948 grafts to HEK293 cells transfected with human full-length PD-1 was measured by flow cytometry. Data is presented as geomean of PD-1 antibody associated fluorescence.
FIG. 13 shows an alignment of the light chains for the murine, acceptor frameworks and humanised light chains and an alignment of the heavy chains for the murine, acceptor frameworks and humanised heavy chains. CDRs are in bold and underlined. Donor residues are in bold, italic and are highlighted.

EXAMPLES

Example 1

Methods for Generation of Anti-PD-1 Antibody Clone 10

The generation of antibody clone 10 has already been described in international application PCT/IB2009/006946 (unpublished).
1.1 Myeloma Cell Line
For fusion the myeloma cell line SP2/0-Ag14 from the German Collection of Microorganisms and Cell Cultures (DSMZ GmbH, Braunschweig) was used. This cell line is a hybrid between BALB/c spleen cells and the myeloma cell line P3x63Ag8. The cells have been described as not synthesizing or secreting immunoglobulin chains, being resistant to 8-azaguanine at 20 µg/ml, and not growing in HAT (Hypoxanthine, Aminopterin, Thymidine) medium. The SP2/0 cells are routinely maintained in tissue culture flasks in standard growth medium (with 10% FCS). A new aliquot of frozen SP2/0 cells was used after a period of 2 weeks in order to avoid the implementation of HGPRT-positive revertants. The myeloma cells were shown to be negative in all mycoplasma tests.
1.2 Antigens for Immunization and Screening
The recombinant protein PD-1Fc was prepared using the methods described for the production of CD28Fc (Evans et al. *Nat. Immunol.* 6, 271-9 (2005)) and concentrated to 5.1 mg/ml in 0.01 M HEPES, 150 mM NaCl, pH 7.4. SDS-PAGE analysis of the antigen run under reducing and non-reducing conditions established the purity of the protein to be >95%.
1.3 Immunization
Five mice (about 8 weeks old) were immunized via the intraperitoneal cavity using an immunization protocol over 60 days. For immunization an alum precipitate of the immunogen was prepared. The alum precipitate was freshly prepared for each boost. The mice were immunized with 50 µg protein and boosted with 25 µg protein. Three mice were used for fusion.
1.4 General Handling of Cells
Cells were handled under sterile conditions using a laminar air-flow system, sterile materials and sterile solutions. Cells were incubated at 37° C. in a humid atmosphere containing 5% carbon dioxide. For cultivation of the hybridoma cells a complete growth medium (CGM) containing DMEM with supplements 2-mercaptoethanol, L-Glutamine, GlutaMax, HT, non essential amino acids, sodium pyruvate, antibiotics/antimycotic solution (in concentrations recommended by the supplier) and FCS at different concentrations (10%, 15% or 20%) was used.
1.5 Preparation of Spleen Cells and Cell Fusions
After asphyxiation of the three immunized mice in $CO_2$ spleens were aseptically removed. A single cell suspension of pooled spleens was prepared. The spleen cells and the myeloma cells were washed several times with DMEM and fused twice in the presence of 1 ml 50% (w/v) PEG 3550 (ratio spleen cells to SP2/0 2.5:1 and 2.4:1). The hybridomas produced were resuspended in CGM containing 20% FCS and aminopterin (HAT medium). The cell suspension (140 Cl/well) of each fusion was plated out into eight 96-well tissue culture flat-bottom plates (Corning-Costar) containing 140 Cl/well peritoneal exudate cells as feeder cells in CGM with 20% FCS. The plates were incubated for 10 days. During this period cells were fed two times with HAT medium. An aliquot of the spleen cell preparation (about $8 \times 10^6$ spleen cells) was cultivated 10 days in a well of a 24-well plate and the cell culture supernatant served as positive control in ELISA.
1.6 Screening Assay
An ELISA was used for screening of IgG in cell culture supernatants. 96 well flat-bottom polystyrene microtiter plates (Greiner, Cat. No 655061) were coated with 50 µl/well PD-1Fc antigen (5 µg/ml) in 0.5 M carbonate/bicarbonate buffer, pH 9.6. After incubation overnight in a moist chamber at 4° C. the plates were washed with tris-buffered saline (TBS, 50 mM Tris, pH 7.8, 500 mM sodium chloride) containing 0.01% Triton X-100 (washing buffer) and blocked with 200 µl/well 2% FCS in TBS (blocking buffer) for 1 hour at room temperature (RT) on a shaker. The wells were washed with washing buffer and 100 µl cell culture supernatant was added in the appropriate well. Cell culture supernatant from SP 2/0 myeloma cells was used as a negative control. As positive control cell culture supernatant from spleen cell culture was used. The plates were incubated on a shaker for 1 h at RT, followed by several washes. For detection of bound antibodies plates were incubated with 50 µl/well goat anti-mouse IgG (Fab specific) conjugated to alkaline phosphatase (1:5000) in blocking buffer for 1 h at RT on a shaker, followed by several washes and addition of 150 µl/well substrate buffer (2 mM 4-nitrophenyl phosphate in 5% diethanolamine+0.5 mM $MgCl_2$, pH 9.8). The optical density (OD) was estimated in a 12-channel Dynex Opsys MR microplate reader at 405 nm. Wells with OD405 nm 2-fold higher than the OD405 nm of the average plate value were selected as positive.

1.7 Selection of Stable Antibody Producers

Cells from positive IgG producing cultures were transferred into wells of a 48-well plate and cultivated for several days (depending on the growth characteristics of the cells). An ELISA on PD-1Fc and without precoated antigen in order to select the specific binders was carried out. The cells from ELISA-positive wells were frozen in freezing medium (90% FCS, 10% DMSO). An aliquot of the cells was further cultivated for production of cell culture supernatants for further characterization.

1.8 Limiting Dilution Cloning

As soon as positive wells were identified, hybridoma cells were cloned to reduce the risk of overgrowth by non-producing cells (first cloning). To ensure that the antibodies are truly monoclonal the hybridomas were cloned again (second cloning). The method of limiting dilution was used for both cloning procedures. IgG producing cells were distributed into one 96 well plate containing feeder cells at a density of 1-3 cells per well. After 8-10 days (depending on growth characteristics) all plates were visually inspected under the microscope for detection of monoclonal growth. Culture supernatants from such wells were screened for specific immunoglobulin content using the above-described screening assay. The appropriate clones concerning growth characteristic and ELISA signal were selected, transferred into wells of a 24-well plate and cultivated for some days. A screening assay was performed. This procedure was repeated two to three times. The appropriate subclone was selected respectively for the second cloning procedure or cultivation for cryopreservation. This procedure resulted in the production of an anti-PD-1 antibody known as Clone 10.

1.9 Preparation and Isotyping of Antibodies

Hybridoma supernatant was prepared and diluted into sterile, azide-free PBS. Purified stocks of monoclonal antibodies were isotyped at 1 μg/ml in PBS using the IsoStrip Mouse Monoclonal Antibody Isotyping Kit (Santa Cruz; sc-24958). Clone 10 was found to be isotype $IgG_{1K}$.

1.10 Sequencing of Clone 10

The genes encoding clone 10 were cloned and sequenced and are provided in FIG. 1. This antibody was named antibody CA051_00948 (often abbreviated to 948).

Example 2

Humanisation of Antibody CA051_00948

Antibody CA051_00948 was humanised by grafting the complementarity determining regions (CDRs) from the mouse antibody V-regions onto human germline antibody V-region frameworks. In order to recover the activity of the antibody, a number of framework residues from the mouse V-regions were also retained in the humanised sequence. These residues were selected using the protocol outlined by Adair et al. (1991) (Humanised antibodies. WO91/09967). Alignments of the mouse antibody (donor) V-region sequences with the human germline antibody (acceptor) V-region sequences are shown in FIG. 13, together with the designed humanised sequence.

The CDRs grafted from the donor to the acceptor sequence are as defined by Kabat (Kabat et al. Sequence of proteins of immunological interest (1987). Bethesda Md., National Institutes of Health, US), with the exception of CDR-H1 where the combined Chothia/Kabat definition is used (see Adair et al. (1991) Humanised antibodies. WO91/09967).

Human V-region VH4 3-1 4-30.4 plus JH4 J-region (V BASE, http://vbase.mrc-cpe.cam.ac.uk/) was chosen as the acceptor for the heavy chain CDRs. The heavy chain framework residues are all from the human germline gene, with the exception of residues 25, 44, 48 and 71 (Kabat numbering), where the donor residues Threonine (T25), Lysine (K44), Methionine (M48) and Arginine (R71) were retained, respectively. The Glutamine residue at position 1 of the human framework was replaced with Glutamic acid (E1) to afford the expression and purification of a homogeneous product: the conversion of Glutamine to pyroGlutamate at the N-terminus of antibodies and antibody fragments is widely reported.

Human V-region VK2 4-1-(1) A18 plus JK2 J-region (V BASE, http://vbase.mrc-cpe.cam.ac.uk/) was chosen as the acceptor for the light chain CDRs. The light chain framework residues are all from the human germline gene, with the exception of residues 2, 3, 45, 62 and 87 (Kabat numbering), where the donor residues Valine (V2), Leucine (L3), Lysine (K44), Isoleucine (I62) and Phenylalanine (F87) were retained, respectively.

Genes encoding the 948.g1 light and heavy chain V-region sequences were designed and constructed by an automated synthesis approach by Entelechon GmbH. The 948.g1 light chain V-region gene sequence was cloned into the UCB-Celltech human light chain expression vector pKH10.1, which contains DNA encoding the human Kappa chain constant region (Km3 allotype). The 948.g1 heavy chain V-region gene sequence was cloned into the UCB-Celltech human gamma-4 heavy chain expression vector pVhγ4P FL, which contains DNA encoding the human gamma-4 heavy chain constant region with the hinge stabilising mutation S241P (Angal et al., Mol. Immunol. 1993, 30(1):105-8). Transient co-transfection of light and heavy chain vectors into HEK293 suspension cells was achieved using 293 Fectin (12347-019 Invitrogen), and gave expression of the recombinant antibody, 948.g1.

The sequences are provided in FIGS. 3-11 and in FIG. 13.

Summary of Ab948 Residues for Humanization

Light Chain

| Kabat position | Human residue to replace donor |
|---|---|
| 4 | Isoleucine |
| 5 | Valine |
| 46 | Glutamine |
| 63 | Phenylalanine |
| 88 | Tyrosine |

Heavy Chain

| Kabat position | Human residue to replace donor |
|---|---|
| 26 | Serine |
| 45 | Glycine |
| 49 | Isoleucine |
| 71 | Valine |

OR
Light Chain

| Kabat position | Human residue to replace donor |
|---|---|
| 2 | Isoleucine |
| 3 | Valine |
| 45 | Glutamine |
| 62 | Phenylalanine |
| 87 | Tyrosine |

Heavy Chain

| Kabat position | Human residue to replace donor |
|---|---|
| 25 | Serine |
| 44 | Glycine |
| 48 | Isoleucine |
| 71 | Valine |

Example 3

Characterisation of the Humanised Antibodies Generated in Example 2

3.1 Flow Cytometry Analysis of Antibody 948 Chimeric and 948 Humanised Graft Binding to Cell-Expressed Human PD-1

In order to determine if humanising antibody 948 had changed its ability to bind PD-1, a binding comparison was performed of 948 (murine parental), 948 chimeric and the 948 humanised graft on HEK293 cells expressing human PD-1.

Method

HEK293 cells were transiently transfected by culturing at $5\times10^6$/well with 5 µg human PD-1 DNA and 293 fectin (Invitrogen) overnight in 6 well plates. The following day PD-1 expressing HEK293 cells were incubated for 1 hr at 4° C. with the stated concentrations of 948 chimeric, 948 humanised graft, 948 chimeric (purified) or 948 murine parental (purified) antibodies. Cells were washed with PBS and incubated with an appropriate secondary antibody, either FITC Mouse anti Human IgG (05-4211 Zymed, 1:20 dilution) or rat anti Mouse IgG (04-6111 Zymed, 1:20 dilution) for 1 hr at 4° C. Flow cytometry analysis was performed on a FACSCalibur (Becton Dickinson).

Results

The flow cytometry binding curves shown in FIG. 12 demonstrate that all versions of antibody 948 bound specifically to cell-expressed PD-1 and that the humanised graft of 948 bound human PD-1 with equal or greater efficiency to the parental and chimeric versions of the antibody.

It will of course be understood that the present invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

The invention claimed is:

1. A humanised agonistic antibody which binds human PD-1 comprising a heavy chain wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3 and the heavy chain framework region is human sub-group sequence VH4 3-1 4-30.4+JH4 (SEQ ID NO: 33) or a derivative thereof wherein up to four residues are changed.

2. A humanised antibody according to claim 1 wherein the residue at at least one of positions 25, 44, 48 and 71 of the variable domain of the heavy chain, as numbered according to Kabat, is a donor residue.

3. A humanised antibody according to claim 2 having the heavy chain variable domain sequence given in SEQ ID NO:23.

4. The antibody of claim 1 further comprising a light chain wherein the variable domain of the light chain comprises the sequence given in SEQ ID NO:4 for CDR-L1, the sequence given in SEQ ID NO:5 for CDR-L2 and the sequence given in SEQ ID NO:6 for CDR-L3 and the light chain framework region is human sub-group sequence VK2 4-1-1 A18+JK2 (SEQ ID NO:31) or a derivative thereof wherein up to five residues are changed.

5. A humanised antibody according to claim 4 wherein the residue at at least one of positions 2, 3, 45, 62, and 87 of the variable domain of the light chain, as numbered according to Kabat, is a donor residue.

6. A humanised antibody according to claim 5 having the light chain variable domain sequence given in SEQ ID NO:15.

7. The antibody of claim 1 having a heavy chain comprising a sequence given in SEQ ID NO:23 and a light chain comprising a sequence given in SEQ ID NO:15.

8. An agonistic antibody molecule according to any one of claims 1, 4, or 7, wherein the antibody molecule is selected from the group consisting of: a complete antibody molecule having full length heavy and light chains, an Fab, Fab', F(ab')$_2$, Fv, VH, VL and scFv fragment.

9. A humanised agonistic antibody which binds human PD-1, wherein the variable domain of the light chain comprises a sequence having at least 95% identity to a light chain variable domain comprising a sequence given in SEQ ID NO:15 and wherein the variable domain of the heavy chain comprises a sequence having at least 95% identity to a heavy chain variable domain comprising a sequence given in SEQ ID NO:23.

10. An isolated DNA sequence encoding the heavy and/or light chain(s) of an antibody according to any one of claims 1, 4, or 7.

11. A cloning or expression vector comprising one or more DNA sequences according to claim 10.

12. A cultured host cell comprising one or more cloning or expression vectors according to claim 11.

13. A process for the production of the antibody comprising culturing the host cell of claim 12 and isolating the antibody.

14. The antibody according to claim 8, wherein the antibody is conjugated to one or more effector molecules.

15. A pharmaceutical composition comprising an antibody according to any one of claims 1, 4, 7, or 14 in combination with one or more of a pharmaceutically acceptable excipient, diluent or carrier.

16. A pharmaceutical composition according to claim 15, additionally comprising other active ingredients.

17. The pharmaceutical composition according to claim 16, wherein the active ingredients are selected from the group consisting of: an antibody, anti-TNF, anti-IL-1β, anti-T cell, anti-IFNγ, anti-LPS, a xanthine, a corticosteroid, fluticasone propionate, a beta-2-agonist, salbutamol, salmeterol, formoterol, an inhibitor of cell growth and proliferation, rapamycin, cyclophosphamide, methotrexate, a CD28 inhibitor and a CD40 inhibitor.

* * * * *

UNITED STATES PATENT AND TRADEMARK OFFICE
CERTIFICATE OF CORRECTION

| | | |
|---|---|---|
| PATENT NO. | : 8,993,731 B2 | Page 1 of 1 |
| APPLICATION NO. | : 13/583999 | |
| DATED | : March 31, 2015 | |
| INVENTOR(S) | : Tyson | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 16 days.

Signed and Sealed this
Twenty-fourth Day of November, 2015

Michelle K. Lee
*Director of the United States Patent and Trademark Office*